(12) United States Patent
Justis et al.

(10) Patent No.: US 7,947,046 B2
(45) Date of Patent: May 24, 2011

(54) ANCHOR EXTENDERS FOR MINIMALLY INVASIVE SURGICAL PROCEDURES

(75) Inventors: Jeff R. Justis, Collierville, TN (US); John D. Pond, Jr., Germantown, TN (US); Larry T. McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1006 days.

(21) Appl. No.: 11/820,964

(22) Filed: Jun. 21, 2007

(65) Prior Publication Data
US 2008/0319477 A1    Dec. 25, 2008

(51) Int. Cl.
*A61B 17/70* (2006.01)

(52) U.S. Cl. ....... 606/86 A; 606/264; 606/265; 606/300; 606/305

(58) Field of Classification Search ................ 606/86 A, 606/99, 300, 305–308
See application file for complete search history.

(56) References Cited

U.S. PATENT DOCUMENTS

| | | | |
|---|---|---|---|
| 4,448,191 A | 5/1984 | Rodnyansky | |
| 5,020,519 A | 6/1991 | Hayes | |
| 5,242,443 A | 9/1993 | Kambin | |
| 5,720,751 A | 2/1998 | Jackson | |
| 5,910,141 A | 6/1999 | Morrison et al. | |
| 6,183,472 B1* | 2/2001 | Lutz | 606/86 A |
| 6,226,548 B1 | 5/2001 | Foley et al. | |
| 6,235,028 B1 | 5/2001 | Brumfield et al. | |
| 6,485,491 B1 | 11/2002 | Farris et al. | |
| 6,530,929 B1 | 3/2003 | Justis et al. | |
| 6,648,888 B1 | 11/2003 | Shluzas | |
| 6,660,006 B2 | 12/2003 | Markworth et al. | |
| 6,740,089 B2 | 5/2004 | Haider | |
| 6,821,277 B2 | 11/2004 | Teitelbaum et al. | |
| 2002/0161368 A1* | 10/2002 | Foley et al. ..................... | 606/61 |
| 2003/0199884 A1 | 10/2003 | Davison et al. | |
| 2003/0225408 A1 | 12/2003 | Nichols et al. | |
| 2003/0229347 A1* | 12/2003 | Sherman et al. ................ | 606/61 |
| 2004/0039384 A1 | 2/2004 | Boehm, Jr. et al. | |
| 2004/0049191 A1 | 3/2004 | Markworth et al. | |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2004/0215190 A1 | 10/2004 | Nguyen et al. | |
| 2004/0267275 A1 | 12/2004 | Cournoyer et al. | |

(Continued)

OTHER PUBLICATIONS

U.S. Appl. No. 11/348,999, filed Feb. 7, 2006, Justis et al.

*Primary Examiner* — Eduardo C Robert
*Assistant Examiner* — Ellen C Hammond

(57) ABSTRACT

Systems for positioning a connecting element adjacent the spinal column in minimally invasive surgical procedures include one or more extenders removably engaged to one or more anchors engaged to a bony segment. The anchor extenders provide a reference to the respective anchor locations within the patient even when the anchor is obstructed by skin and/or tissue of the patient. An inserter can be movably mounted to the one or more anchor extenders, or an inserter can be employed without mounting to the one or more anchor extenders. In either form, the inserter is operable to position a stabilization element relative to the anchors for engagement to the anchors to stabilize the bony segment to which the anchors are engaged. At least one of the one or more anchor extenders includes a reduction assembly that is operable to move one or more portions of the bony segment while maintaining the minimally invasive character of the procedure.

17 Claims, 16 Drawing Sheets

U.S. PATENT DOCUMENTS

| | | |
|---|---|---|
| 2005/0010219 A1 | 1/2005 | Dalton |
| 2005/0010221 A1 | 1/2005 | Dalton |
| 2005/0033299 A1 | 2/2005 | Shluzas |
| 2005/0080418 A1 | 4/2005 | Simonson et al. |
| 2005/0085813 A1 | 4/2005 | Spitler et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0154389 A1 | 7/2005 | Selover et al. |
| 2005/0171540 A1 | 8/2005 | Lim et al. |
| 2005/0182407 A1 | 8/2005 | Dalton |
| 2005/0192570 A1 | 9/2005 | Jackson |
| 2005/0192575 A1* | 9/2005 | Pacheco .................. 606/61 |
| 2005/0192579 A1 | 9/2005 | Jackson |
| 2005/0192589 A1 | 9/2005 | Raymond et al. |
| 2006/0074418 A1* | 4/2006 | Jackson .................. 606/61 |
| 2007/0049931 A1 | 3/2007 | Justis et al. |
| 2007/0213714 A1* | 9/2007 | Justis .................. 606/61 |

* cited by examiner

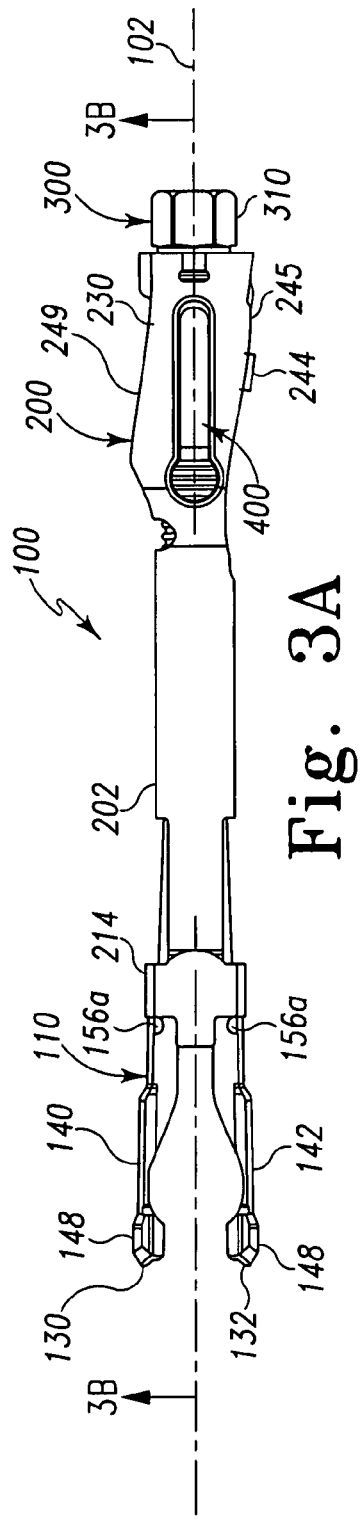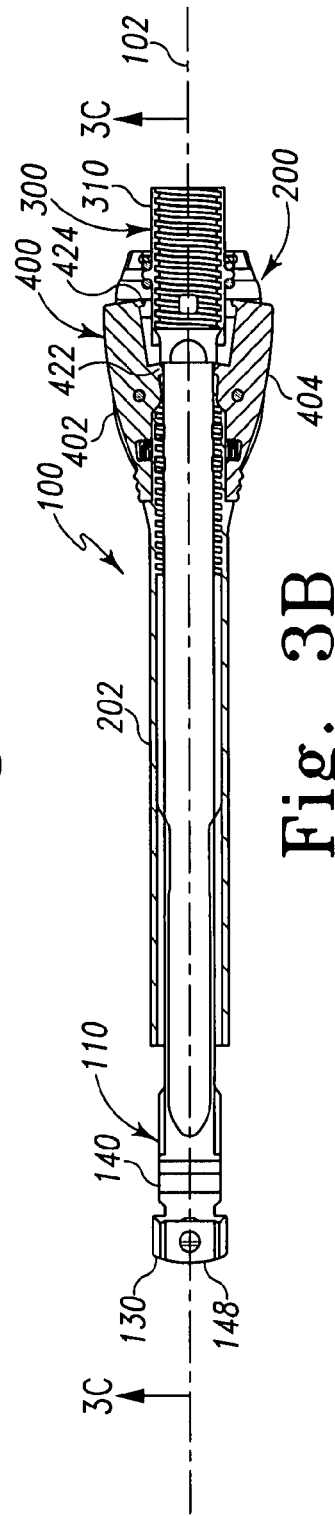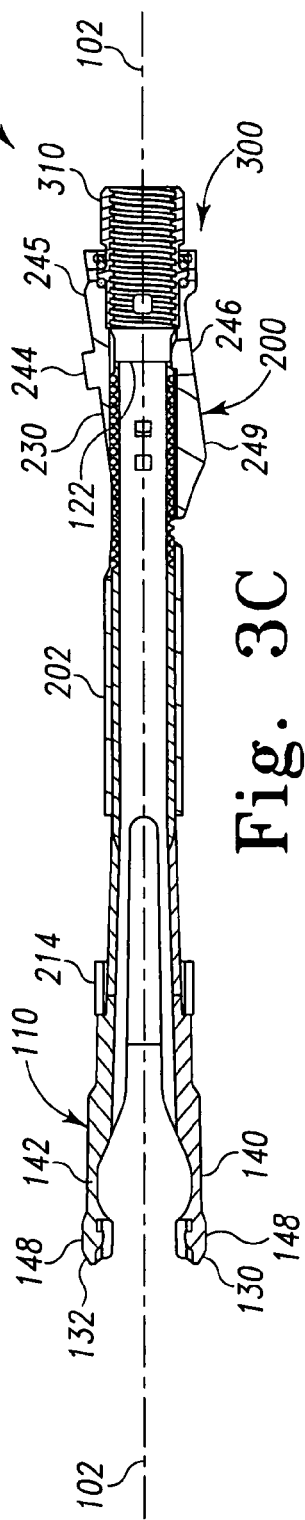

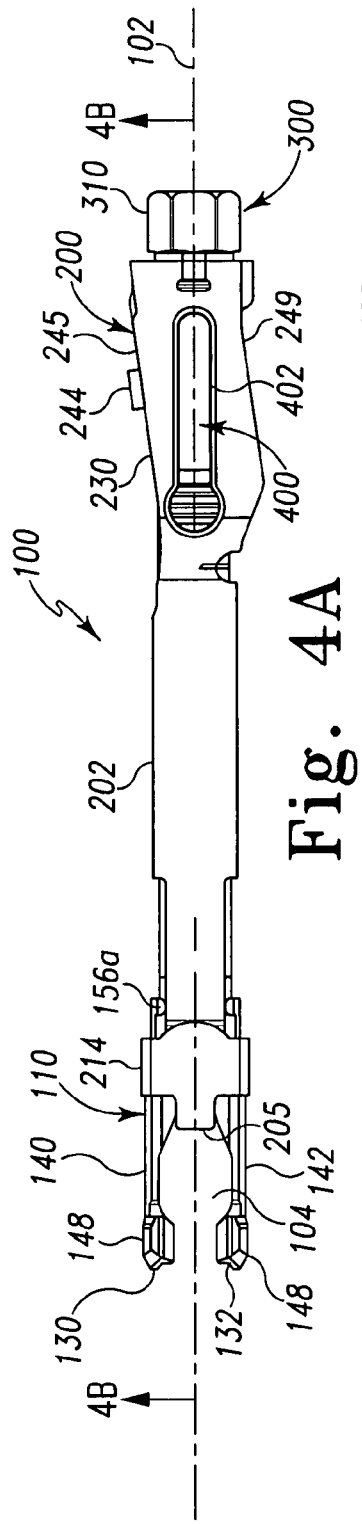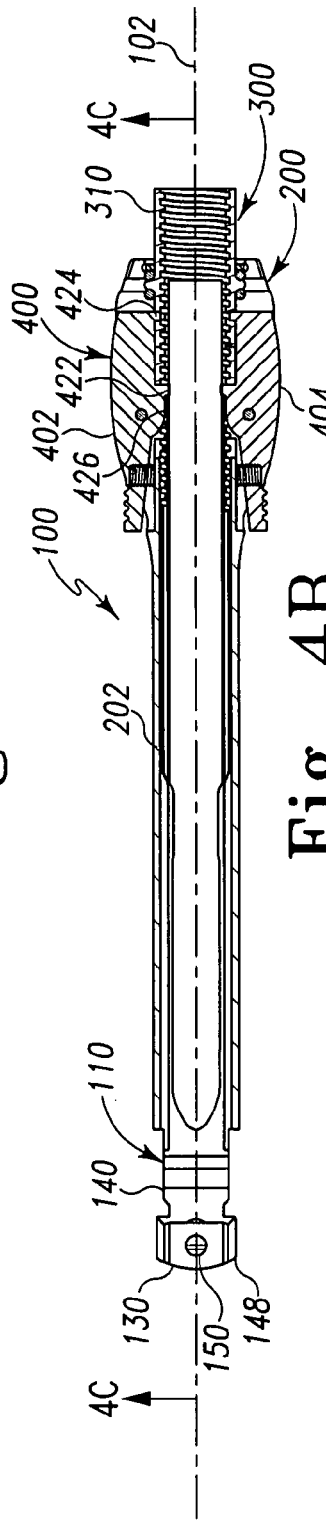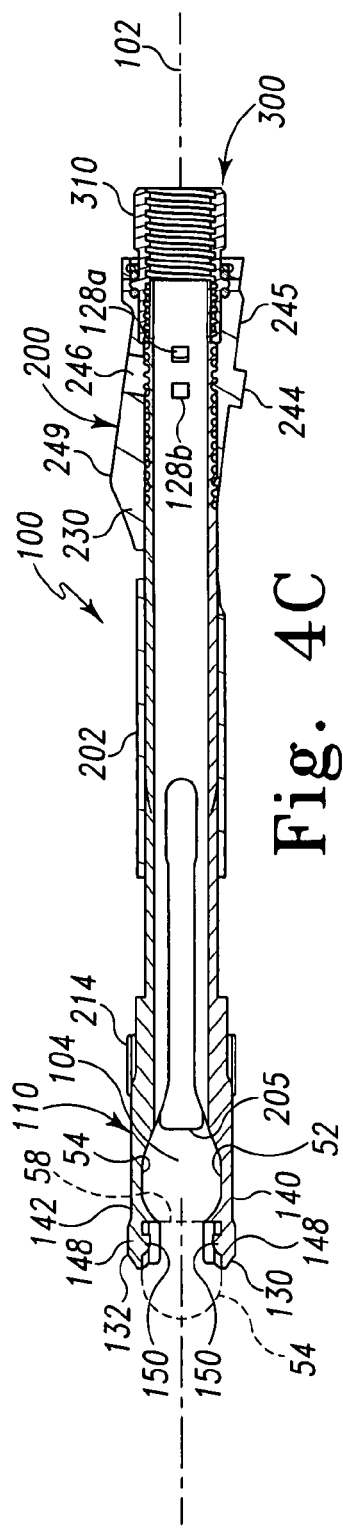

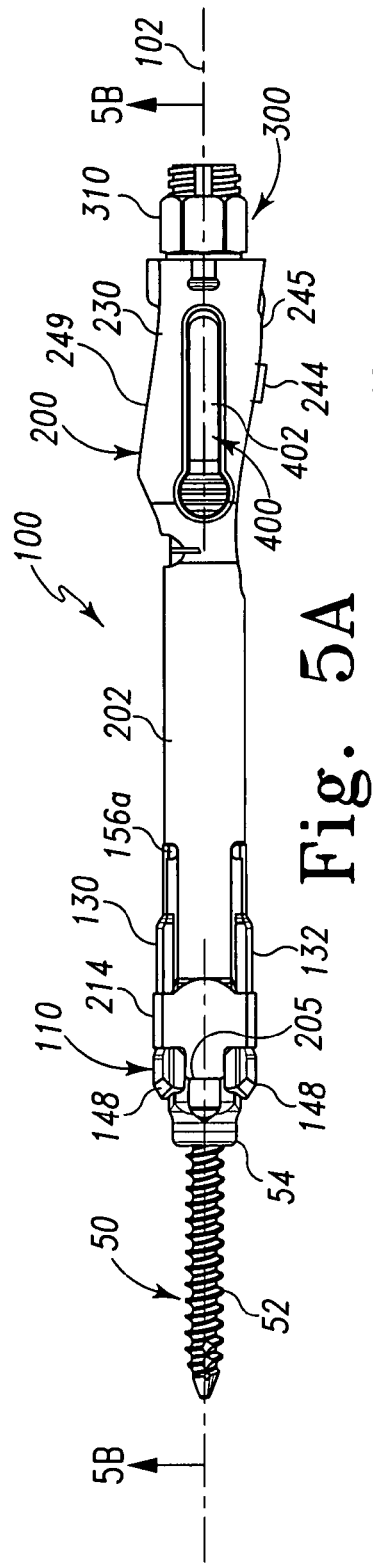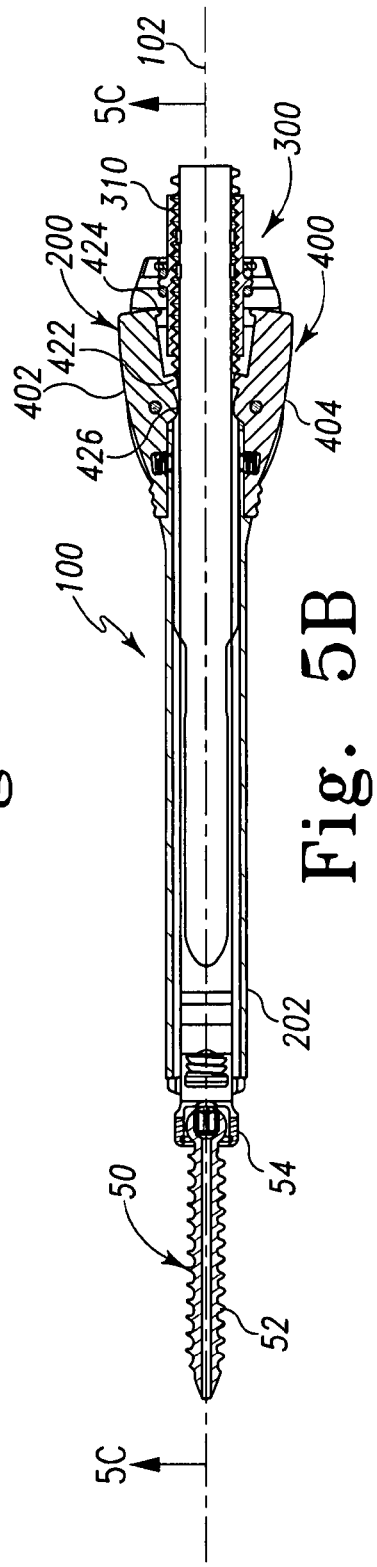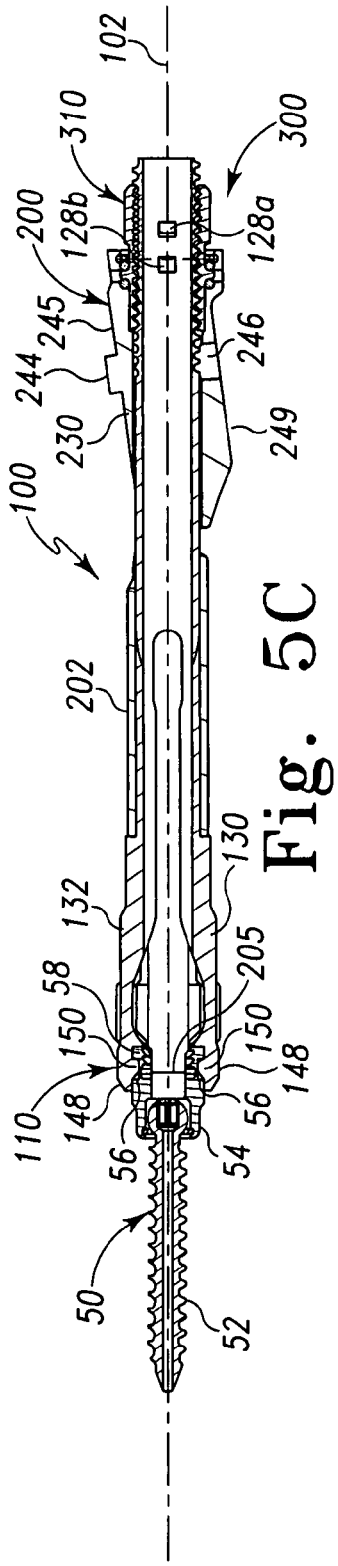

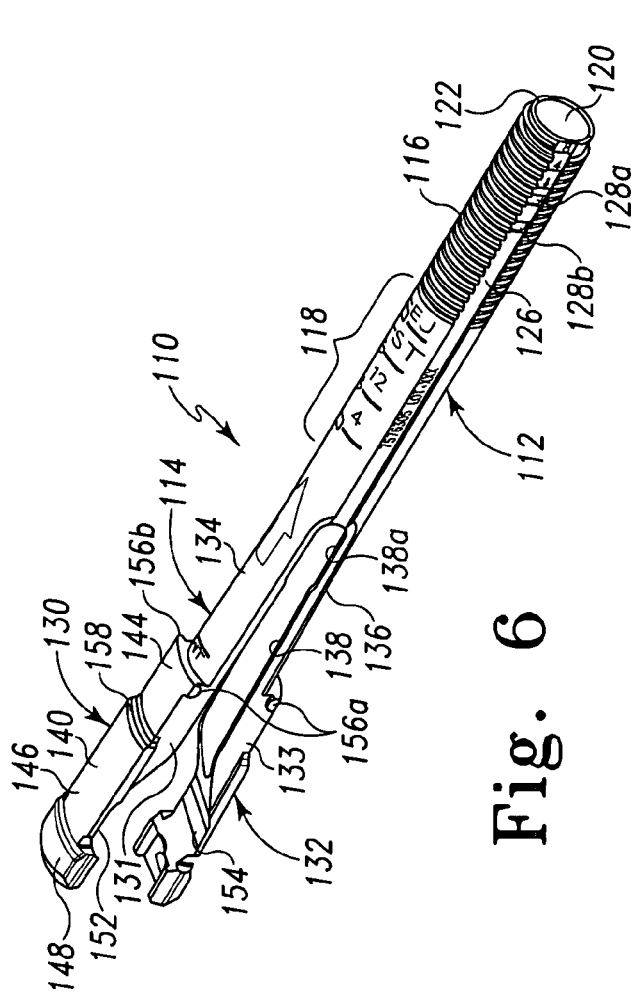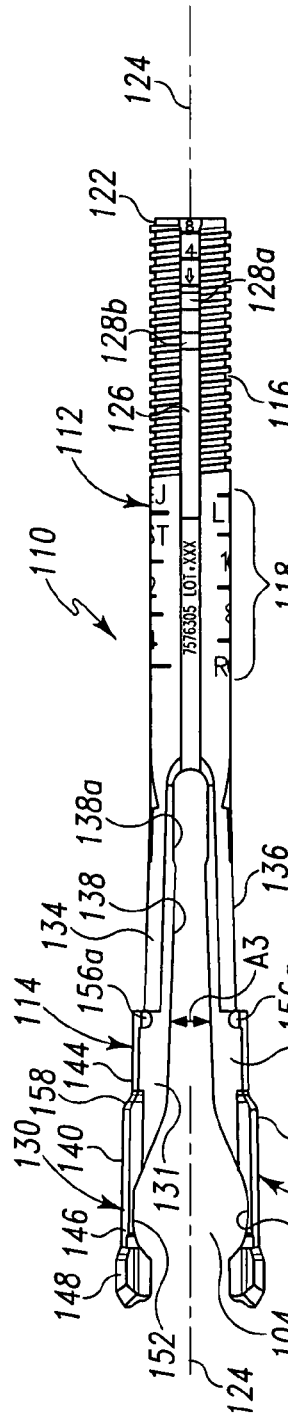
Fig. 6
Fig. 7

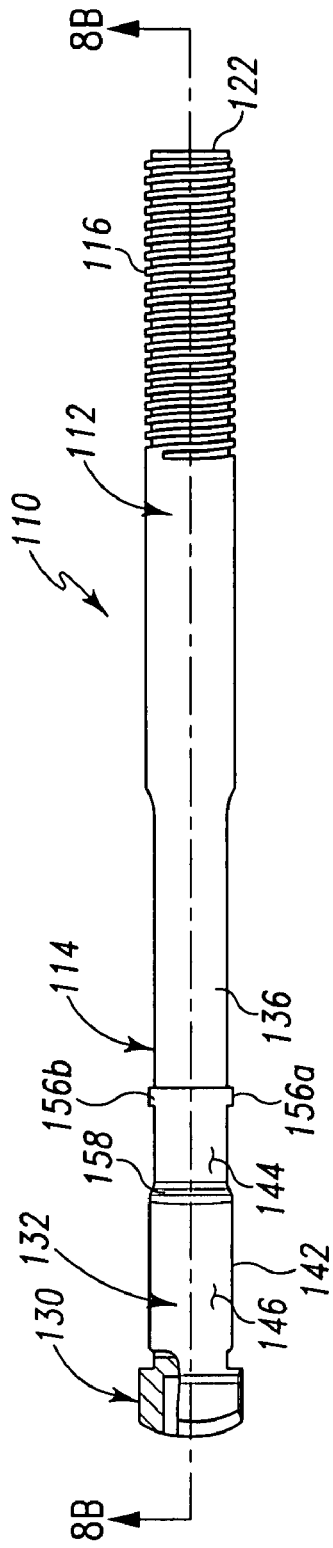
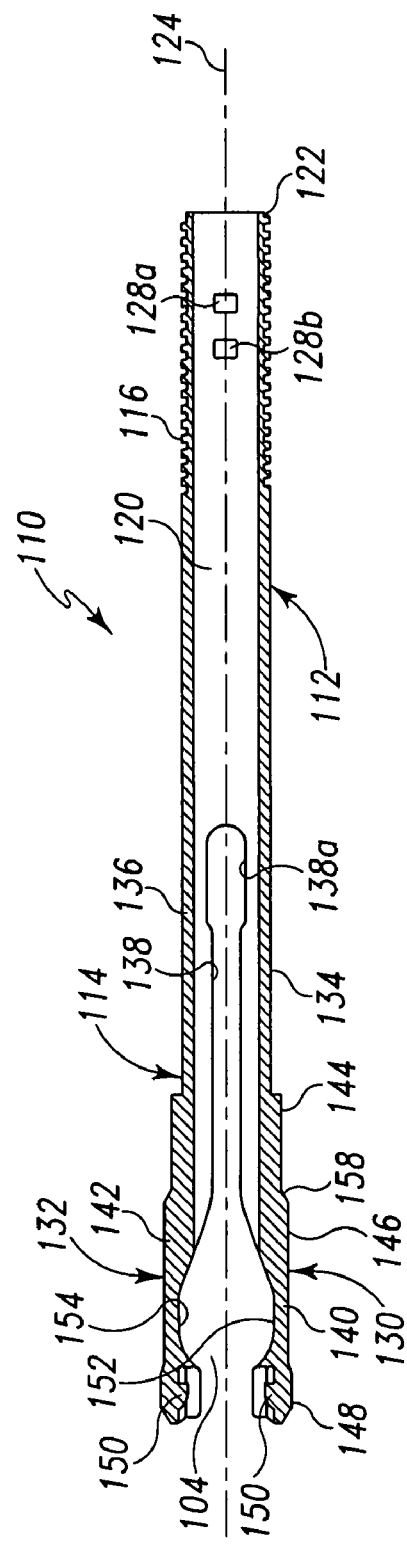
Fig. 8A
Fig. 8B

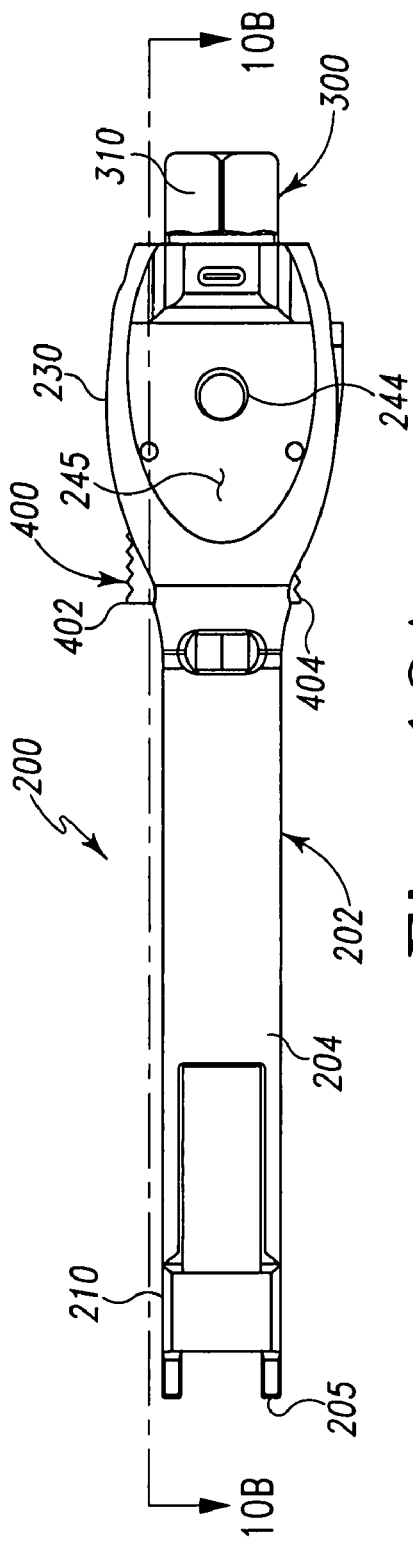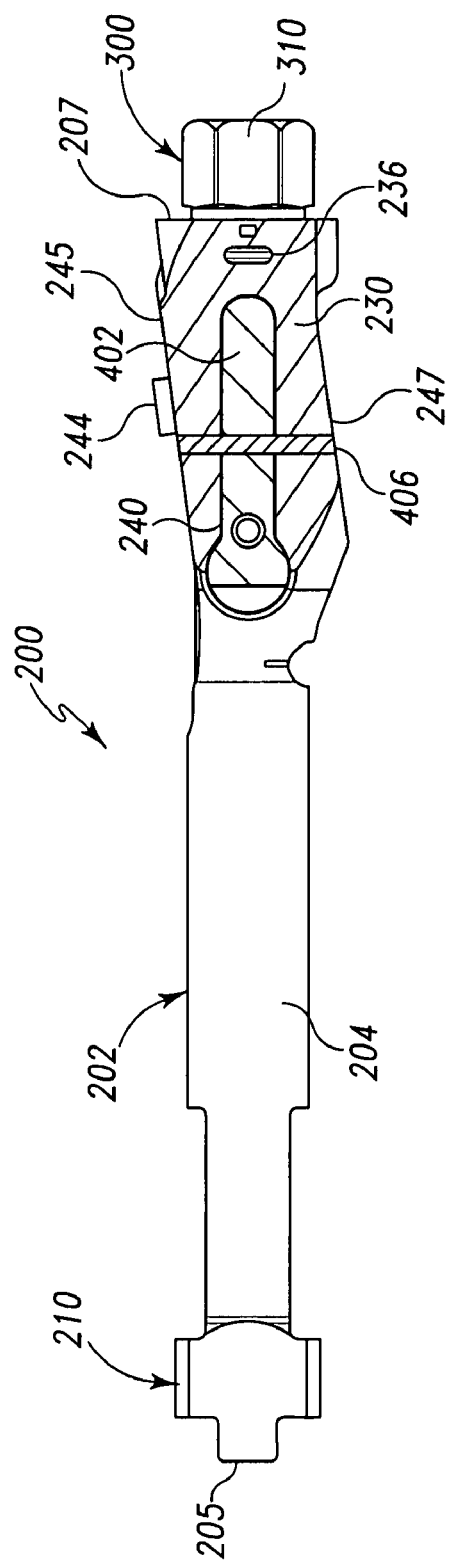
Fig. 10A
Fig. 10B

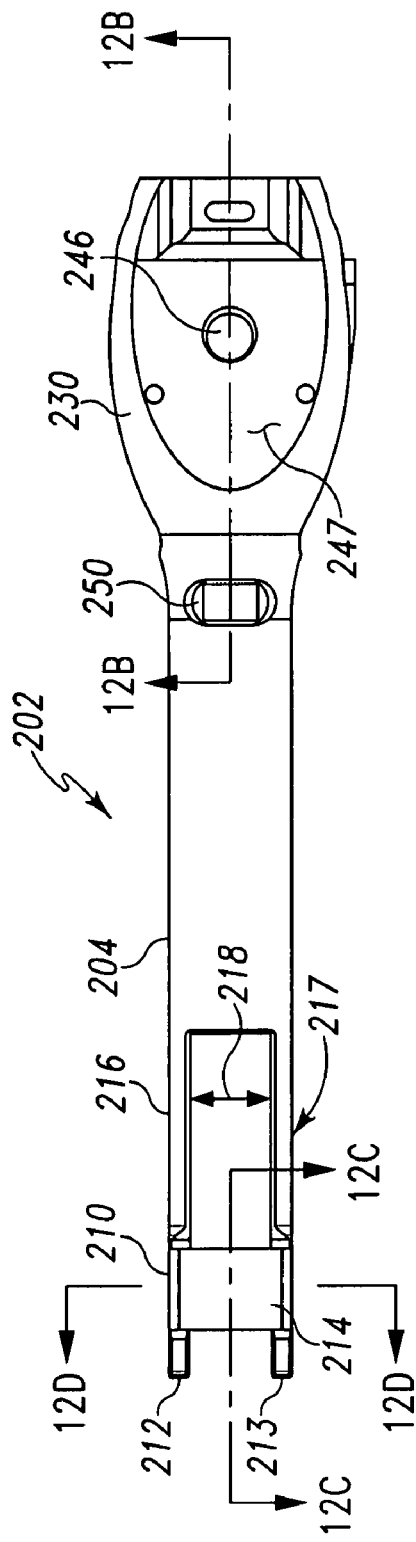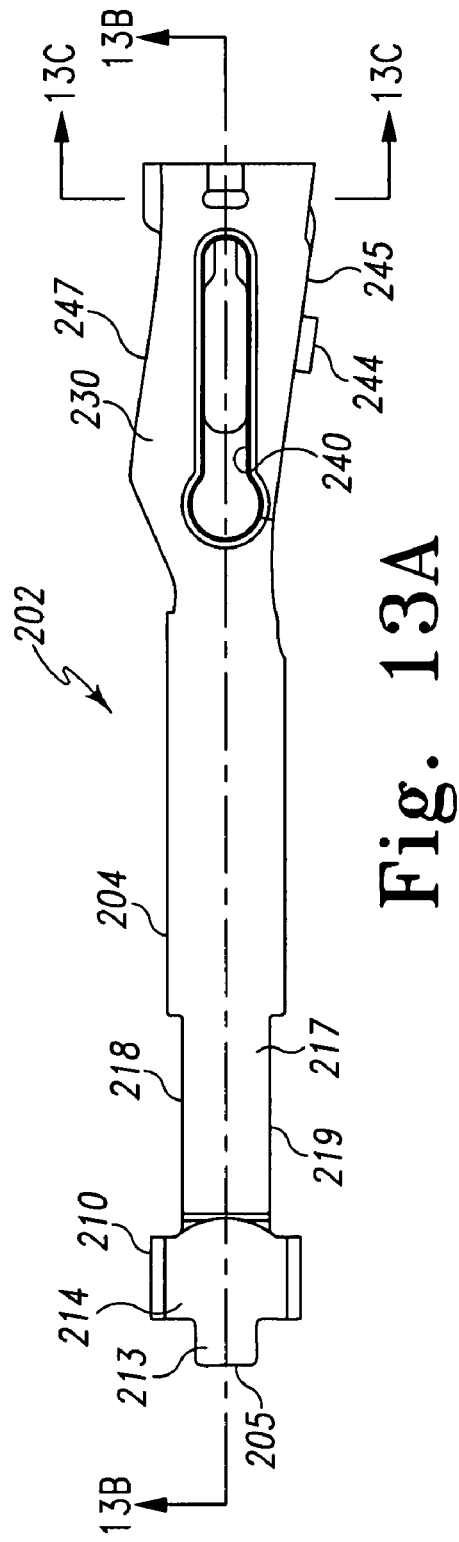
Fig. 12A
Fig. 13A

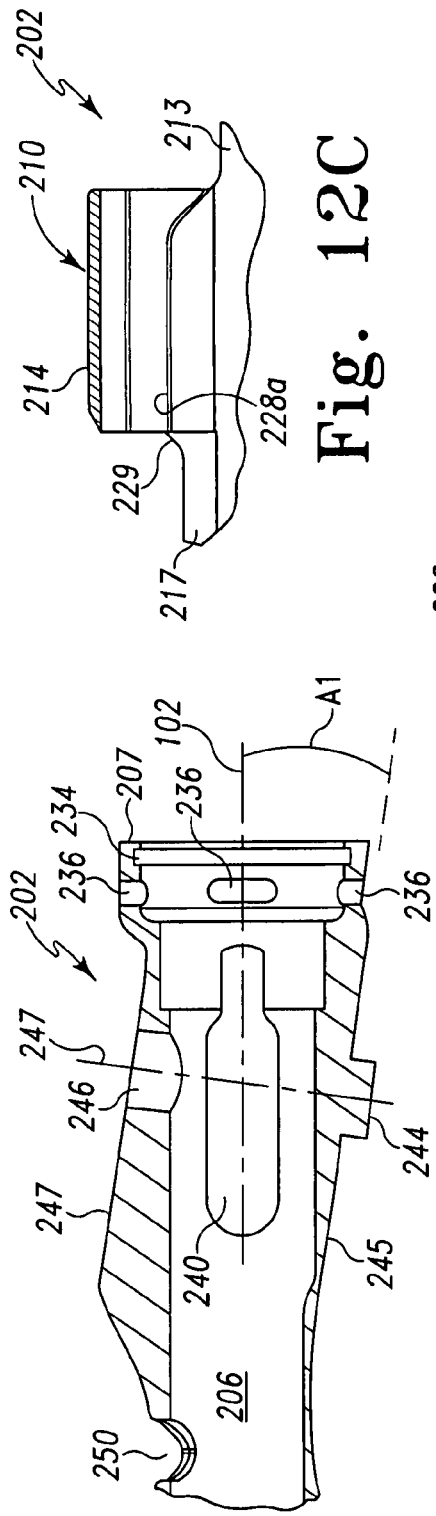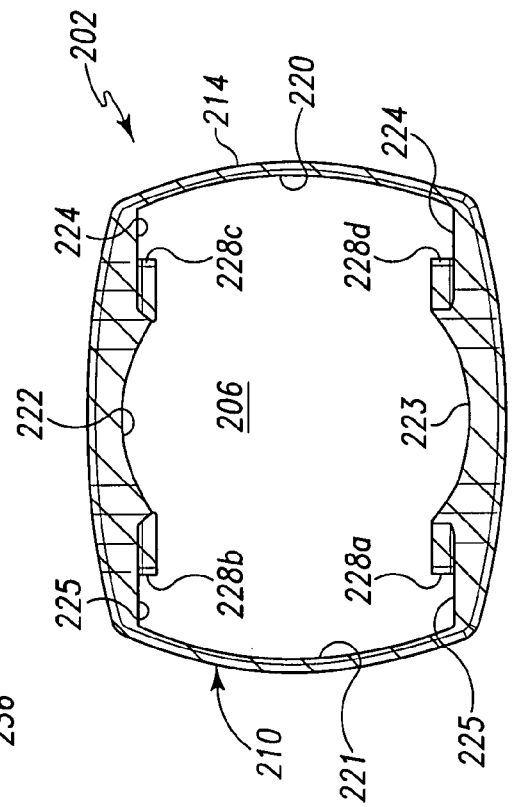

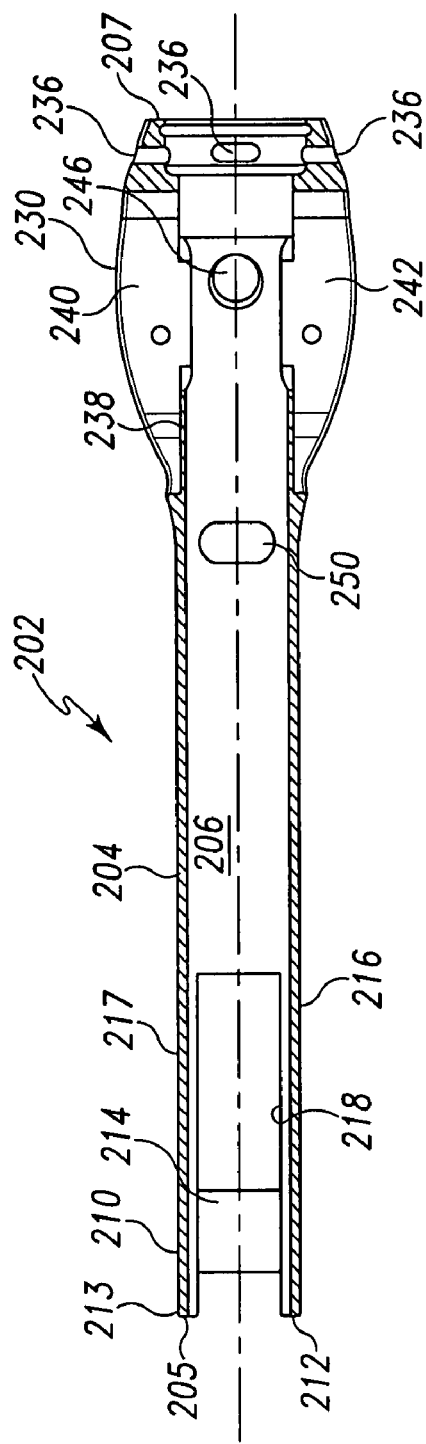
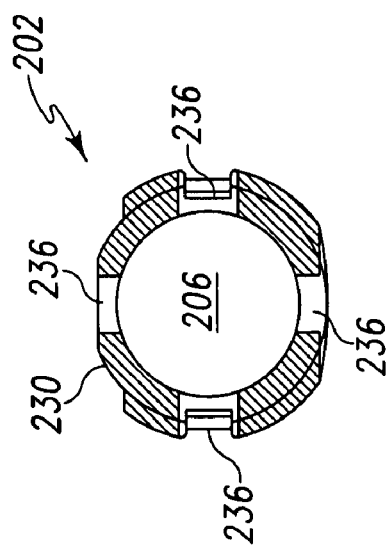
Fig. 13B
Fig. 13C

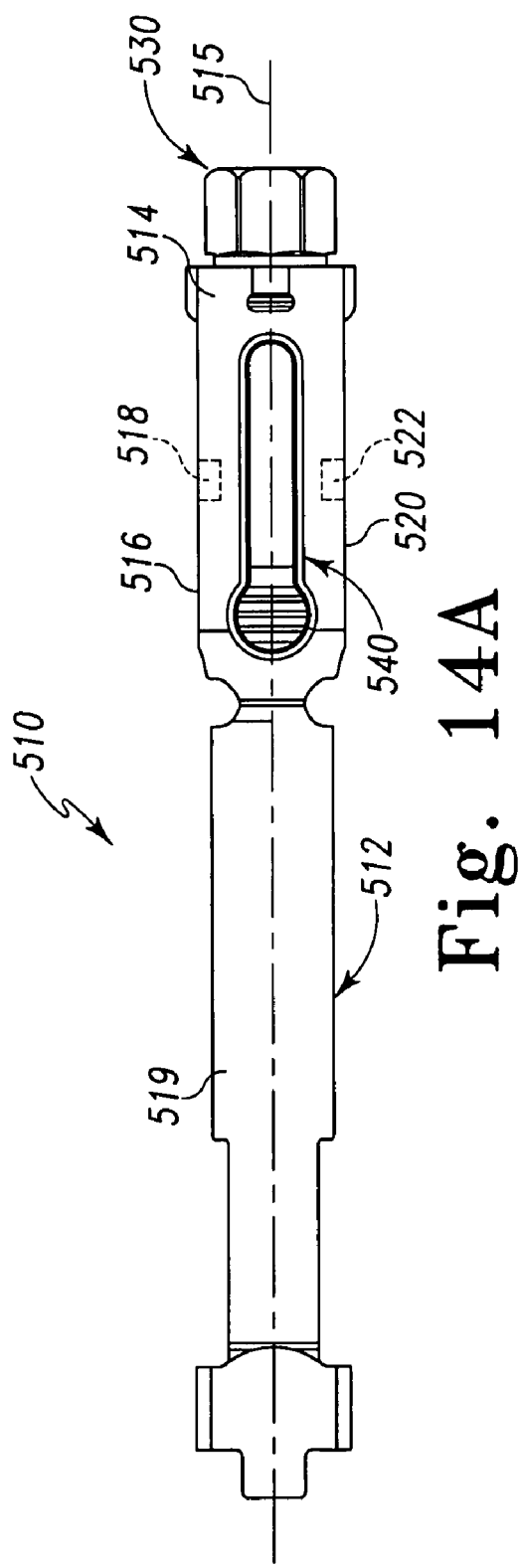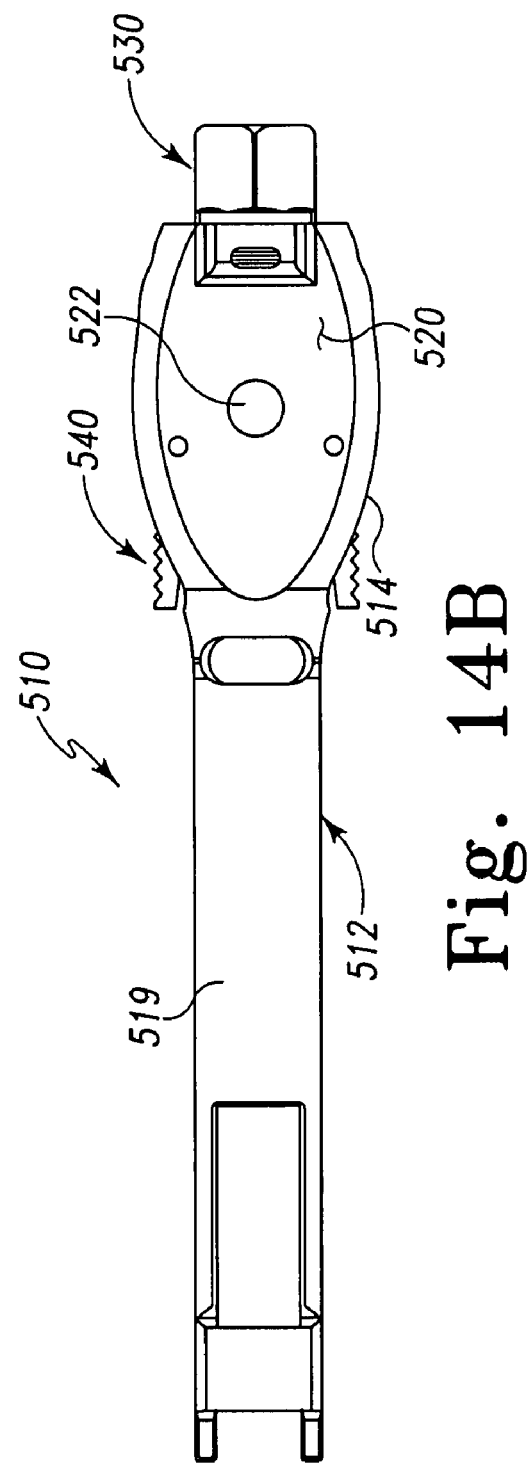
Fig. 14A
Fig. 14B

ANCHOR EXTENDERS FOR MINIMALLY INVASIVE SURGICAL PROCEDURES

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. There remains a need for further improvements instruments and methods for stabilizing bony structures using minimally invasive techniques.

SUMMARY

Systems for positioning a connecting element adjacent the spinal column in minimally invasive surgical procedures include one or more extenders removably engaged to one or more anchors engaged to a bony segment. The anchor extenders provide a reference to the respective anchor locations within the patient even when the anchor is obstructed by skin and/or tissue of the patient. An inserter can be movably mounted to the one or more anchor extenders, or employed without mounting to the one or more anchor extenders. In either form, the inserter is operable to position a stabilization element relative to the anchors for engagement to the anchors to stabilize the bony segment to which the anchors are engaged. At least one of the one or more anchor extenders includes a reduction assembly that is operable to move one or more portions of the bony segment while maintaining the minimally invasive character of the procedure.

In one embodiment, at least one of the anchor extenders includes an outer member configured with a proximal female portion and at least one other anchor extender is configured with a proximal male portion so that the male and female portions mate with one another when the distal ends of the anchor extenders are mounted to anchors.

In another embodiment, at least one of the anchor extenders includes an outer member configured with a proximal portion configured to be positioned between and engaged to the proximal portions at least two other anchor extenders when the distal ends of the anchor extenders are mounted to anchors.

In one embodiment, an anchor extender is provided with an inner member and an outer member around the inner member. A reduction assembly is connected between the inner and outer members. The reduction assembly includes an actuating member mounted to the outer member and threadingly engaged to the inner member. The actuating member is operable to axially move the inner and outer members relative to one another to displace a bony segment mounted to the anchor extender. In a further embodiment, a positive stop arrangement between the inner and outer members prevents the inner member from rotating relative to the outer member as the inner and outer members are axially displaced relative to one another.

In another embodiment, an anchor extender is provided with an inner member and an outer member around the inner member. The inner and outer members are axially moveable relative to one another between a first position to permit anchor engagement between first and second arms at the distal end of the inner member and a second position where the outer member contacts the inner member and positively engages to first and second arms to actively clamp the first and second arms of the inner member to the anchor.

In another embodiment, an anchor extender is provided with an inner member and an outer member around the inner member. The inner and outer members are axially moveable relative to one another between a first position to permit anchor engagement to the inner member, a second position where the inner member is engaged to an anchor at its distal end, and a plurality of third positions where the inner and outer members are axially displaced to provide reduction of a bony segment engaged to the anchor. The inner member includes indicia visible through the outer member to provide an indication of the positioning the inner and outer members at the first, second and plurality of third locations.

In yet another embodiment, an anchor extender is provided with an inner member engageable to an anchor at its distal end, and an outer member around the inner member. A locking assembly is provided that selectively locks and releases the inner and outer members relative to one another. The locking assembly is also configured to maintain one or more relative axial positionings of the inner and outer members when the reduction assembly is employed to displace the inner and outer members relative to one another.

Related features, aspects, embodiments, objects and advantages of the present invention will be apparent from the following description.

BRIEF DESCRIPTION OF THE DRAWINGS

FIG. 3A is an elevation view of an extender useable with the systems of FIGS. 1 and 2 with the extender in a fully extended condition.

FIG. 3B is a section view of the extender of FIG. 3A along line 3B-3B.

FIG. 3C is a section view of the extender of FIG. 3B along line 3C-3C.

FIG. 4A is an elevation view of an extender useable with the systems of FIGS. 1 and 2 with the extender in an engaged condition to engage an anchor thereto.

FIG. 4B is a section view of the extender of FIG. 4A along line 4B-4B.

FIG. 4C is a section view of the extender of FIG. 4B along line 4C-4C.

FIG. 5A is an elevation view of an extender useable with the systems of FIGS. 1 and 2 with the extender in a fully reduced condition by axially displacing the inner and outer members of the extender relative to one another.

FIG. 5B is a section view of the extender of FIG. 5A along line 5B-5B.

FIG. 5C is a section view of the extender of FIG. 5B along line 5C-5C.

FIG. 6 is a perspective view of an inner member of the extender.

FIG. 7 is an elevation view of the inner member of FIG. 6.

FIG. 8A is an elevation view of the inner member rotated 90 degrees about its longitudinal axis from its FIG. 7 orientation.

FIG. 8B is a section view along line 8B-8B of FIG. 8A.

FIG. 10A is an elevation view of the outer member assembly of FIG. 9.

FIG. 10B is a section view along line 10B-10B of FIG. 10A.

FIG. 12A is an elevation view of an outer member of the outer member assembly of FIG. 9.

FIG. 12B is a section view along line 12B-12B of FIG. 12A.

FIG. 12C is a section view along line 12C-12C of FIG. 12A.

FIG. 12D is a section view along line 12D-12D of FIG. 12A.

FIG. 13A is an elevation view of the outer member of the outer member assembly rotated 90 degrees about its longitudinal axis relative to its FIG. 12A orientation.

FIG. 13B is a section view along line 13B-13B of FIG. 13A.

FIG. 13C is a section view along line 13C-13C of FIG. 13A.

FIG. 14A is an elevation view of another embodiment outer member assembly.

FIG. 14B is an elevation view of the outer member assembly of FIG. 14A rotated 90 degrees about its longitudinal axis.

DESCRIPTION OF THE ILLUSTRATED EMBODIMENTS

Figure 1:
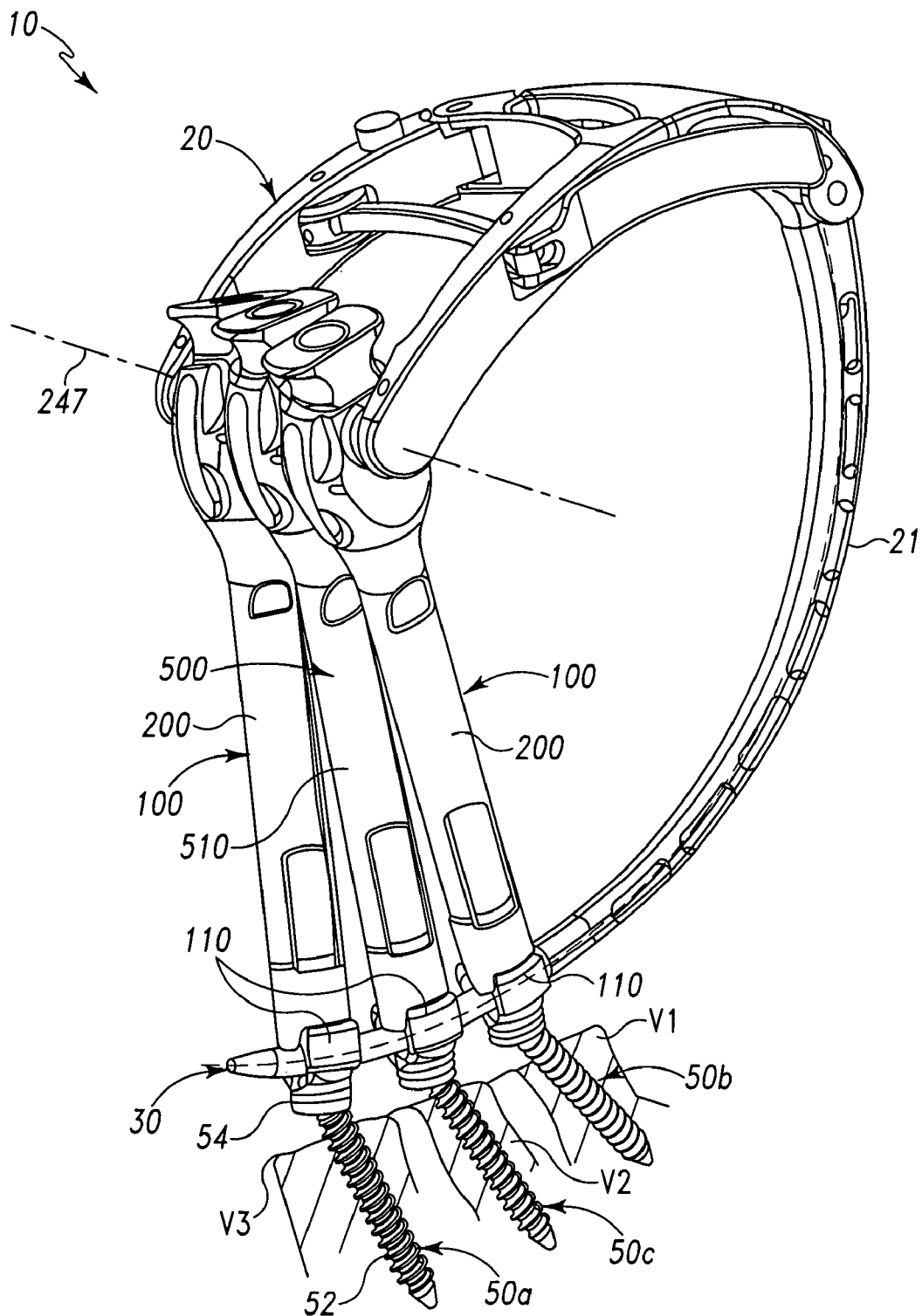
FIG. 1 is a perspective view of a system for positioning a connecting element in a patient in minimally invasive surgical procedures.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Systems and methods for insertion of a connecting element for connection with anchors engaged to bony parts of the body are provided. In one form, the systems include at least one extender extending from at least one anchor engaged to the bony part of the body. An installation instrument is operable to position a connecting element from a location remotely positioned from the at least one anchor to a location adjacent to or within the anchor where the connecting element can be secured to the anchor. The installation instrument can be mounted to the at least one extender adjacent its proximal end, or employed to guide the connecting element without mounting to the at least one extender. The anchor and connecting element can each be positioned into the patient in minimally invasive procedures, minimizing trauma and surgical risks to the patient and promoting rapid post-operative recovery. However, applications in non-minimally invasive surgeries are also contemplated.

The at least one extender includes an elongated inner member engageable to the anchor and an outer member assembly positioned about and engaged to the inner member. The outer member assembly is operable to manipulate the inner member to a first condition or position permitting the anchor to be loaded or ejected from the inner member, a second condition or position where the anchor is securedly engaged to the inner member, and a plurality of reduced conditions or positions where the inner member and outer member assembly are axially displaced relative to one another to manipulate a bony segment engaged to the anchor and/or to position a connecting element into the anchor while the inner member remains engaged to the anchor.

In one embodiment, two or more extenders are engaged to respective ones of two or more anchors. The connecting element is engaged to an inserter that is employed without mounting to the extenders to guide insertion of the connecting element to a location more proximate the anchors. The extenders are manipulated for reduction to align the bony segments and/or to position the connecting element into the anchors. Examples of inserters for connecting elements inserted according to this embodiment may be found in U.S. patent application Ser. No. 11/348,999 filed on Feb. 7, 2006, which is incorporated herein by reference in its entirety.

In another embodiment, at least three extenders are engaged to respective ones of three anchors, such as shown in FIG. 1. In FIG. 1 there is shown a minimally invasive surgical system 10 that includes an installation instrument 20, first and second outer extenders 100, and middle extender 500. Installation instrument 20 is pivotally mounted at one end to the outer lateral sides of outer extenders 500 and at the opposite end is engaged to a connecting element 30. Examples of installation instruments mountable to three or more extenders are found, for example, in U.S. Pat. No. 6,530,929 issued Mar.

11, 2003, and U.S. Patent Application Publication No. 2007/0049931 published Mar. 1, 2007, each of which is incorporated herein by reference in its entirety.

Extenders 100, 500 are releasably mountable to respective ones of the anchors 50a, 50b, 50c (collectively and individually also referred to herein as anchor 50 or anchors 50.) Installation instrument 20 is movable about a pivot axis 247 defined at its coupling location with outer extenders 100. Middle extender 500 includes a proximal end positioned between and secured to each of the outer extenders 100. Movement of installation instrument 20 swings inserter arm 21 along an arcuate insertion path toward the anchors 50. Connecting element 30, engaged to the distal end of inserter arm 21, is guided toward anchors 50 along the insertion path where it is then engaged to anchor 50 to provide stabilization of the bony segment to which anchors 50 are engaged.

Outer extenders 100 and components thereof are shown and discussed further below with reference to FIG. 3A to FIG. 13C. Middle extender 500 is substantially identical to outer extenders 100, except it includes a proximal hub portion 514 (FIGS. 14A-14B) adapted to engage outer extenders 100, while outer extenders 100 include a proximal hub portion 230 adapted to engage middle extender 500 and installation instrument 20. Middle extender 500 includes an inner member that is identical to inner member 110 shown and described with reference to FIG. 3A to FIG. 7. Middle extender also includes an outer member assembly 510, as shown in FIGS. 14A-14B, that is positioned around inner member 110.

Middle outer member assembly 510 includes an outer member 512 with proximal hub portion 514 and tubular body portion 519 extending distally from proximal hub portion 514. Hub portion 514 includes a first side with abutment surface 516 having a first receptacle 518, and a second side with an abutment surface 520 with a second receptacle 522. First and second abutment surfaces 516, 520 each have a generally flat profile and extend parallel to one another and to longitudinal axis 515. A reduction assembly 530 mounted to proximal hub portion 514 couples inner member 110 to outer member 512 and provides the capability to axially move inner member 110 relative to outer member 512 while inner member 110 is engaged to anchor 50. A locking assembly 540 mounted to hub portion 514 is engageable to inner member 110 to maintain a relative axial positioning of inner member 110 relative to outer member 512.

Figure 9:
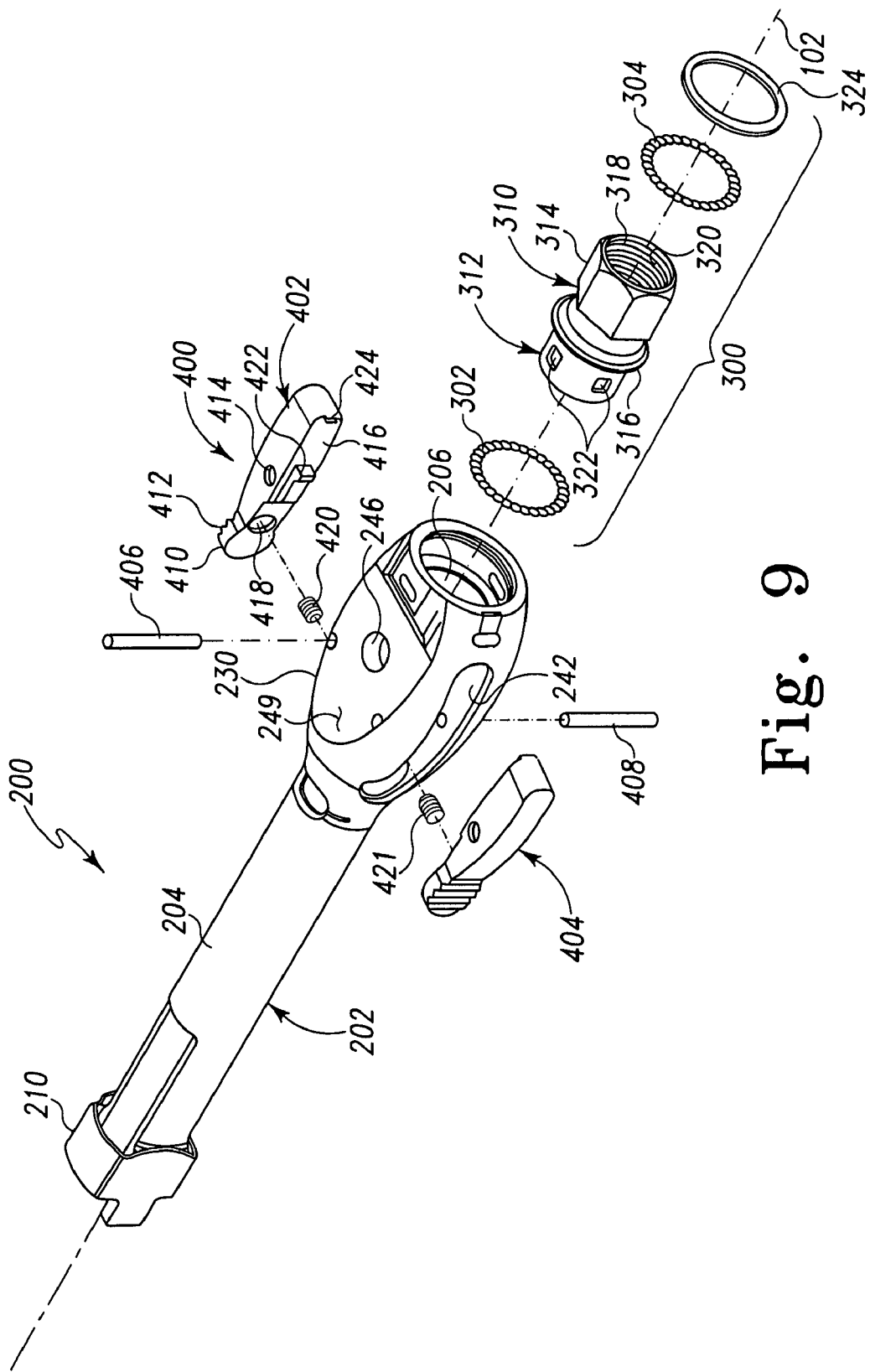
FIG. 9 is an exploded perspective view of an outer member assembly of the extender.
Figure 11A:
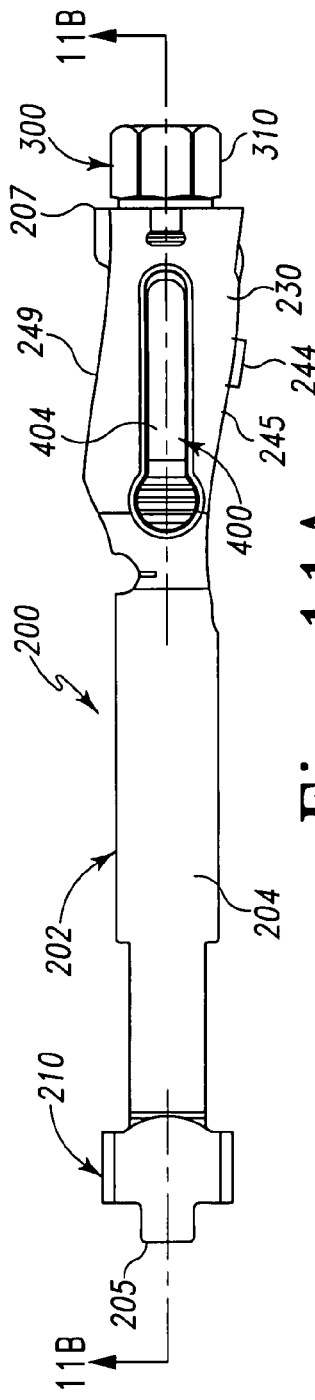
FIG. 11A is an elevation view of the outer member assembly of FIG. 9 rotated 90 degrees about its longitudinal axis from its FIG. 10A orientation.

As shown in FIGS. 9, 10A and 11A, outer extender 100 includes outer member assembly 200 with outer member 202. Outer member 202 includes a proximal hub portion 230 with a first side forming an abutment surface 245 and an opposite second side with a mounting surface 249. As also shown in FIG. 12B, an extension member 244 extends outwardly from abutment surface 245 along pivot axis 247, and a receptacle 246 extends into mounting surface 249 along pivot axis 247. Extension members 244 from adjacent sides of a pair of outer extenders 100 are received in respective ones of first and second receptacles 518, 522 of proximal hub portion 514 to couple the pair of outer extenders 100 to opposite sides of middle extender 500. Installation instrument 20 is rotatably mounted to receptacles 246 in the outer lateral sides of the outer extenders 100 so that the installation instrument is pivotal about pivot axis 247 relative to extenders 100, 500. Abutment surface 245 and mounting surface 249 extend parallel to one another and at an angle A1 to longitudinal axis 102. In one embodiment, angle A1 is about 8 degrees. The non-parallel orientation of surfaces 245, 249 facilitates positioning of abutment surfaces 245 in abutting engagement with an adjacent one of the abutment surfaces 516, 520 of middle extender 500 when outer extenders 100 are pivoted by manipulating receiving portion 54 of the anchors 50 mounted to outer extenders 100. The non-parallel orientation of the abutment surfaces 245 with longitudinal axis 102 provides abutting engagement when the longitudinal axes 102 of outer extenders 100 are in non-parallel relation with longitudinal axis 515 of middle extender 500 created by manipulating the orientation of receiving portion 54 relative to bone engaging portion 52 of the respective anchor 50 while maintaining receiving portions 54 in alignment with one another to receive connecting element 30.

Figure 2:
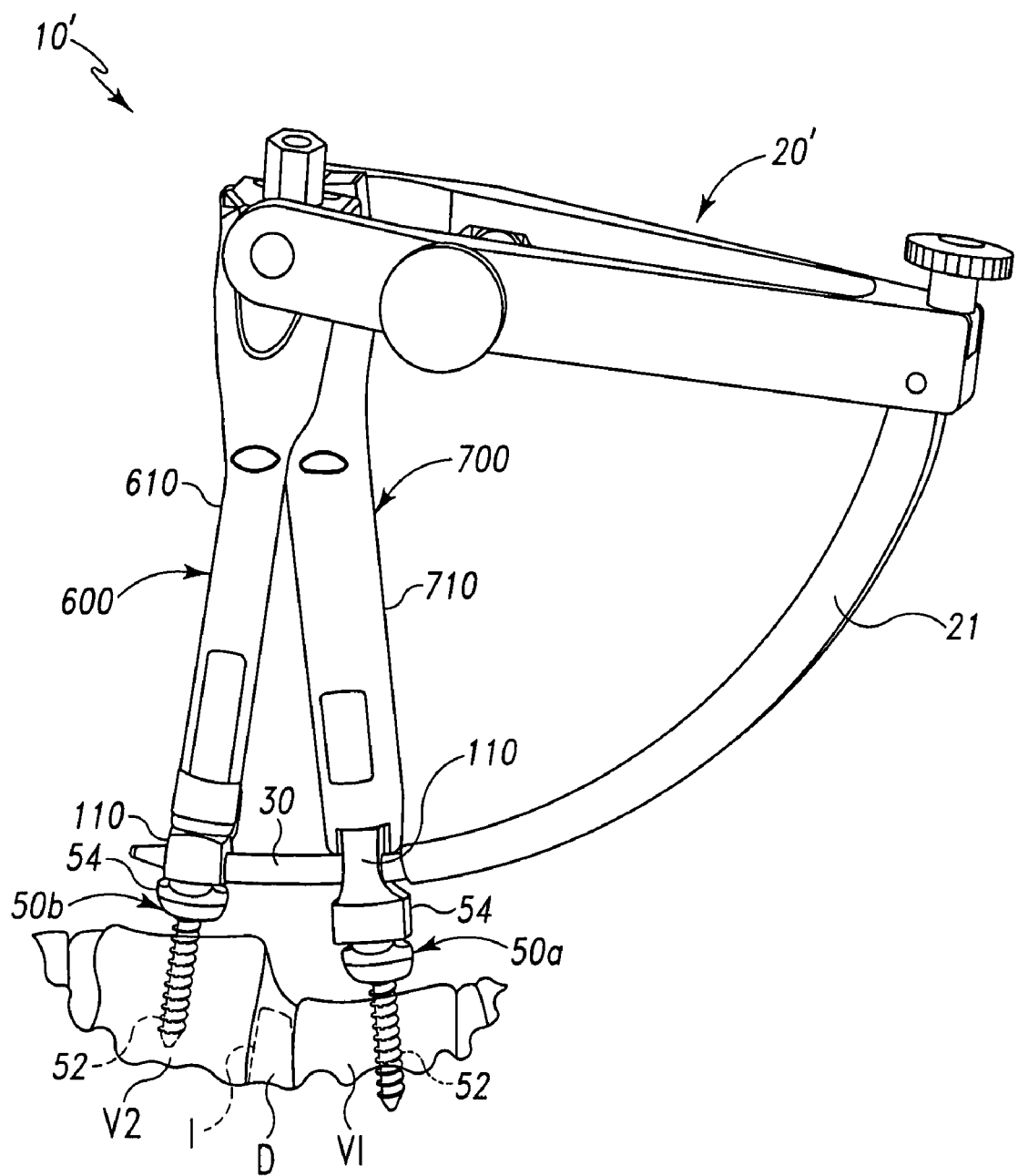
FIG. 2 is a perspective view of another embodiment system for positioning a connecting element in a patient in a minimally invasive procedure.

In another embodiment, at least two extenders are engaged to respective ones of two anchors, such as shown in FIG. 2. In FIG. 2 there is shown a minimally invasive surgical system 10' that includes an installation instrument 20', a male extender 600, and a female extender 700. Installation instrument 20' is pivotally mounted at one end to extenders 600, 700 and at an opposite end to connecting element 30. Examples of installation instruments mountable to at least one or more extender are found, for example, in U.S. Pat. No. 6,530,929 issued Mar. 11, 2003, and U.S. Patent Application Publication No. 2005/0171540 published Aug. 4, 2005, each of which is incorporated herein by reference in its entirety.

Extenders 600, 700 are releasably mountable to respective ones of the anchors 50a, 50b engaged to vertebrae V1, V2. Installation instrument 20' is movable about a pivot axis defined at its coupling location with extenders 600, 700. In one embodiment, movement of installation instrument 20' swings inserter arm 21' along an arcuate insertion path toward the anchors 50a, 50b. Connecting element 30, engaged to the distal end of inserter arm 21', is guided toward anchors 50a, 50b where it is attached between anchors 50a, 50b.

Male and female extenders 600, 700 are substantially identical to outer extender 100 discussed further below, except male and female extenders 600, 700 include outer member assemblies 610, 710, shown in FIGS. 15A-16B, with proximal hub portions 614, 714, respectively, that are adapted to couple to one another and to installation instrument 20'. Male outer member 612 and female outer member 712 each include a tubular body portion 619, 719, respectively, that extends distally from the respective hub portion 614, 714 along longitudinal axis 615, 715. The outer member assemblies 610, 710, of extenders 600, 700 receive an inner member such as inner member 110 discussed below and shown in FIG. 3A to FIG. 7.

Outer member assemblies 610, 710 are coupled to the inner member 110 with reduction assemblies 630, 730. Reduction assemblies 630, 730 are identical to reduction assembly 300 discussed below. Hub portion 614 includes a first side with planar abutment surface 616 having extension 618 extending laterally therefrom and transversely to longitudinal axis 615. Hub portion 614 also includes a second side 620 opposite abutment surface 616 that includes a laterally extending portion 622. Laterally extending portion 622 includes outwardly tapered sidewall 624 extending to a lateral mounting surface 626 that is parallel to abutment surface 616. One side of installation instrument 20' is rotatably mounted to laterally extending portion 622 at mounting surface 626. A receptacle or other structure can be provided in or extend from mounting surface 626 to facilitate coupling with installation instrument 20'.

Female outer member assembly 710 includes proximal hub portion 714 that has a first side with a planar abutment surface 716 including receptacle 718 formed therein transversely to longitudinal axis 715. Hub portion 714 includes a second side 720 with a laterally extending portion 722. Laterally extending portion 722 includes outwardly tapered sidewall 724 that extends to a mounting surface 726 that is parallel to abutment surface 716. The other side of installation instrument 20' is rotatably mounted to laterally extending portion 722 at mounting surface 726. Hub portions 614, 714 are coupled together with extension 618 received in receptacle 718 and with abutment surfaces 616, 716 in abutting engagement with one another. Lateral extending portions 622, 722 provide a mounting platform that is spaced from longitudinal axes 615, 715 sufficiently to allow pivoting movement of the installation instrument 20' about extenders 600, 700 by locating the arms of installation instrument 20' away from outer members 612, 712.

In the illustrated embodiment, the abutment surface 616 and mounting surface 626 are angled at an angle A2 relative to longitudinal axis 615. Also, abutment surface 716 and mounting surface 726 are angled at an angle A2 relative to longitudinal axis 715. In one embodiment, angle A2 is about 4 degrees. The non-parallel orientation of the abutment surfaces with longitudinal axes 615, 715 facilitates positioning of abutment surfaces 616, 716 in contact with one another when the longitudinal axes 615, 715 are in non-parallel relation created by manipulating the orientation of receiving portion 54 relative to bone engaging portion 52 of the respective anchor 50 while maintaining receiving portions 54 in alignment with one another to receive connecting element 30.

In one procedure, at least one vertebra is not in proper alignment with the other vertebrae. Accordingly extenders 100, 500, 600, 700 are provide with reduction assemblies that permit the extender to be manipulated by the surgeon to provide a controlled and measurable displacement of the vertebra to which the manipulated vertebrae is engaged. For example, in FIG. 2 vertebra V1 is not in proper alignment with vertebra V2. Female extender 700 includes reduction assembly 730 that is operable to axially displace inner member 110 relative to outer member 712. Since inner member 110 is coupled to the vertebra V1 through anchor 50a, vertebra V1 is moved into the desired alignment to seat connecting element 30 in anchor 50a.

Male extender 600 is also operable to move vertebra V2 into a desired alignment with reduction assembly 630. In the embodiment of FIG. 1, outer extenders 100 include reduction assemblies 300, and middle extender 500 includes reduction assembly 530, so that any one or all of the vertebrae V1, V2, V3 can be moved by manipulating the extender anchored thereto.

In one procedure, anchors 50 are engaged to two or more vertebrae with extenders extending therefrom. The anchors can be guided into position over guidewires, fluoroscopic visualization, or other minimally invasive surgical technique, to engage the respective vertebra while minimizing trauma to the patient. The installation instrument is then mounted to the extenders, and moved to guide connecting element 30 into position relative to the anchors. In other embodiments, the connecting element is guided via freehand techniques and/or under visualization through fluoroscopy or other imaging system.

As discussed further below, the receiving portions of the anchors need not be initially aligned with one another to receive the connecting element since the extenders define a pathway to receive the connecting element between the proximal end of the anchor and the distal end of the outer member. The connecting element is engaged to at least one of the anchors 50 of a vertebra that is in a desired alignment. In one embodiment, the connecting element is received in the receiving portion of the anchor, and a set screw or other engaging member is delivered through the passage of the extender to secure the connecting element in the receiving portion. The remaining extenders mounted to anchors not aligned with the anchor engaged to the connecting element are then manipulated via their respective reduction assemblies so that the distal end of the outer member of the manipulated extender contacts the connecting element and the inner member is axially displaced relative to the outer member to move the vertebra engaged by the anchor toward the connecting element until the connecting element is seated in the receiving portion of the moved anchor/vertebra. The connecting element is then secured in the newly aligned vertebra to maintain it in position relative to the other aligned vertebrae. The steps are repeated as needed to align one or more additional vertebrae and secure the aligned vertebrae to the connecting element. After the connecting element is secured to the anchors, the extenders are manipulated with the reduction assembly to axially displace the inner member relative to the outer member to eject the anchor from engagement with the inner member, allowing the extender to be withdrawn from the patient. Either before or after manipulation of the vertebra, a fusion device or other implant I (FIG. 2) can be positioned in one or more of the disc spaces D between adjacent vertebrae.

Connecting element 30 can be an elongated rod or shaft curved along its length with a radius of curvature that corresponds generally to the radius of curvature of inserter arm 21, 21'. However, it should be understood that it is contemplated that connecting element 30 can include any configuration known for a rod, implant, or fastener, so long as connecting element 30 is insertable between two or more anchors. Connecting element 30 can be non-rigid, elastic and/or superelastic and in the form of a cable, band, wire, or artificial ligament that is used in tethering, guiding, or other surgical procedures. Connecting element 30 can be percutaneously or non-percutaneously inserted with the installation instrument to a location adjacent connecting element receiving portions of one or more anchors 50 engaged to a bony structure in the body of an animal subject to stabilize the bony structure.

In the illustrated embodiments, connecting element 30 is a rigid rod curved along an arc that forms an extension of the inserter arm of the installation instrument. However, it is contemplated that connecting element 30 can have a curvature that differs from the curvature of the insertion arm, or can have a curvature that varies or is compounded along its length, or can be linear. Connecting element 30 can be configured for insertion along an insertion axis defined by any one or any combination of mathematical relationships, including, for example, linear, exponential, logarithmic, trigonometric, geometric, parabolic, quadratic, cubic, hyperbolic, elliptic, or parametric relationships.

Anchors 50 include a distal bone engaging portion 52 and proximal connecting element receiving portion 54. In the illustrated embodiment, bone engaging portion 52 is a bone screw with a threaded shank to engage the bony structure of the underlying vertebra or other bony structure. Connecting element receiving portion 54 is a receiver having a pair of opposing arms defining a longitudinal passage alignable along the axis or path along which connecting element 30 is inserted. The arms further define a proximal/distally extending opening that opens at a proximal end of the arms to receive a set screw (not shown), nut or other engaging member to secure connecting element 30 in the passage. Bone engaging portion 52 can be pivotally received in connecting element receiving portion 54 and extend through a distal opening thereof, and structured to interact therewith to provide anchor 50 with multi-axial capabilities that permits either a selected number of positions or infinitely numbered of positions of bone engaging portion 52 relative to connecting element engaging portion 54.

Other forms for anchors 50 are contemplated, including uni-axial and uni-planar forms. The bone engaging portion can be in the form of a spike, staple, fusion device, cannulated screw, fenestrated screw, interbody device, intrabody device, clamp, plate, suture anchor, bolt, pin or other bone engaging member. The connecting element receiving portion can be in the form of a saddle, yoke, eye-bolt or through-hole, side opening member, bottom opening member, top-opening member, eyelet, or any other structure engageable to the connecting element.

FIGS. 3A-5C show various configurations of extender 100 created by manipulating the extender to the desired condition to perform various functions. It should be understood that operation of extenders 500, 600 and 700 is the same as that described for extender 100. Referring to FIGS. 3A-3C, extender 100 is shown in a fully extended position where the proximal end 122 of inner member 110 is spaced distally from actuation member 310 of reduction assembly 300. In the fully extended position, arms 130, 132 of inner member 110 are configured to return toward a normally open position where the arms 130, 132 diverge from one another in a distal direction relative to longitudinal axis 102. Engaging members 148 at the distal ends of arms 130, 132 are spaced so that the receiving portion 54 of anchor 50 can be readily inserted or removed from therebetween without interference. Inner member 110 is freely axially slidable in outer member 202 from the fully extended position to a locked and open condition, as discussed further below.

In FIGS. 4A-4C, extender 100 is manipulated to move inner member 110 axially and proximally relative to outer member assembly 200 to an engaged and locked condition where an anchor, such as anchor 50, is securely engaged between engaging members 148 of first and second arms 130, 132 at the distal end of inner member 110. In the locked condition, anchor 50 is firmly held between distal engaging members 148 of arms 130, 132 of inner member 110. As shown in FIGS. 4C and 5C, engaging members 148 each include a projection 150 that is received in a recess 56 formed in the outer surface of the arms of receiving portion 54 when in the locked condition. As shown in FIG. 4C, the distal end 205 of outer member 202 of outer member assembly 200 is spaced proximally from the proximal end 58 of anchor 50 to provide a pathway 104 between the distal end of outer member 202 and anchor 50. The connecting element 30 is positionable through pathway 104 when, for example, the vertebrae are not aligned with one another. In the illustrated embodiment, arms 130, 132 include concavely curved inner surfaces 152, 154, respectively, that form a widened, tear-dropped shape for pathway 104 that can receive a connecting element having an enlarged portion along its length in comparison to the portions received in receiving portions 54.

In FIGS. 5A-5C, extender 100 is manipulated to further axially move inner member 110 relative to outer member assembly 200 to a reduced position where the distal end 205 of outer member 202 is positioned distally of proximal end 58 of anchor 50. In this position, if the connecting element were inserted into pathway 104 or otherwise located proximally of proximal end 58, the vertebra engaged by anchor 50 is reduced or moved so that connecting element 30 is received in receiving portion 54 by distal end 205.

Extender 100 includes reduction assembly 300 engaged to outer member 202 and inner member 110. Reduction assembly 300 is operable to axially move inner member 110 relative to outer member 202. Extender 100 also include a locking assembly 400 that is mounted to outer member 202 and is releasably engageable to inner member 110 to prevent inner member 110 from being displaced proximally relative to outer member 202 from the locked condition of FIGS. 4A-4C, securing anchor 50 to inner member 110 unless locking assembly 400 is actuated to an unlocked condition, such as shown in FIGS. 3A-3C and FIGS. 5A-5C. The locking engagement of inner member 110 prevents the accidental disengagement of anchor 50 from inner member 110 during manipulation of the extender 100.

Referring now to FIGS. 6-8B, inner member 110 will be further discussed. Inner member 110 includes a proximal tubular body portion 112 and a distal engaging portion 114 extending along a central longitudinal axis 124. Proximal body portion 112 defines a central passage 120 opening at proximal end 122. Passage 120 extends from proximal end 122 and through distal engaging portion 114. Proximal body portion 112 includes an externally threaded end portion 116. Indicia 118 is provided along proximal body portion 112 between threaded end portion 116 and distal engaging portion 114. A longitudinal groove 126 is provided along proximal body portion 112 in the outer surface thereof. Groove 126 interrupts the external threads along threaded end portion 116. Threaded end portion 116 also includes a proximal window 128a and a distal window 128b in groove 126 that each communicate with passage 120.

Distal engaging portion 114 includes a pair of arms 130, 132 extending along longitudinal axis 124. Arms 130, 132 are mirror images of one another, and like components are designated with the same reference numerals. Arms 130, 132 each include a proximal portion 134, 136, respectively, that joins proximal body portion 112. A slot 138 extends between arms 130, 132 in communication with passage 120. Arms 130, 132 are movable toward and away from one another about a living hinge type arrangement with proximal body portion 112 that is formed by slot 138. Slot 138 is provided with a relief portion 138a that increases the size of slot 138 adjacent to body portion 112 to aid flexing of arms 130, 132 about their living hinges. Arms 130, 132 are arranged in non-parallel relation to one another so that arms 130, 132 diverge distally at an angle A3 to facilitate placement of anchor 50 between distal engaging members 148. The distally diverging arms 130, 132 also permit the outer member 202 to positively engage the outer surfaces of arms 130, 132 and actively move the arms 130, 132 toward one another to clamp receiving portion 54 between engaging members 148. Groove 126 extends from proximal end 122 to slot 138.

Arms 130, 132 include distal contact portions 140, 142, respectively, that are contacted by outer member 202 to secure anchor 50 between engaging members 148. Contact portions 140, 142 each include a proximal shoulder 144 along its outer surface that extends along longitudinal axis 124 and a distal shoulder 146 along its outer surface that also extends along longitudinal axis 124. Anchor engaging member 148 extends distally from distal shoulder 146. Anchor engaging member 148 also extends laterally outwardly from distal shoulder 146, and is sized to extend along the width of an arm of receiving portion 54 of anchor 50. Anchor engaging member 148 also includes inner projection 150 extending toward the other arm that is received in a recess of the arm of the anchor 50 to resist anchor 50 from being dislodged from arms 130, 132 when engaged thereto.

Arms 130, 132 include inner surfaces 152, 154, respectively, that are oriented toward one another. Inner surfaces 152, 154 are scalloped or curved away from one another to form pathway 104 between distal shoulders 146. As discussed above, pathway 104 can receive a connecting element therethrough that has an enlarged shape between the portions thereof that are engaged to anchors 50. Proximal shoulders 144 also each include bosses 156a, 156b at the proximal end thereof. As discussed further below, bosses 156a, 156b are engaged by outer member 202 to force arms 130, 132 away from one another to facilitate moving arms 130, 132 away from one another to eject anchor 50 from between engaging members 148. A lip 158 provides a transition between proximal and distal shoulders 144, 146 so that distal shoulder 146 is located laterally outwardly from proximal shoulder 144. As discussed further below, outer member 202 rides along distal shoulder 146 from its proximal end when in the engaged position, as shown in FIGS. 4A-4C, to its distal end when in the fully reduced position, as shown in FIGS. 5A-5C. Outer member 202 contacts distal shoulder 146 of the arms 130, 132 to move arms 130, 132 toward one another and to maintain arms 130, 132 in a position that engages anchor 50 between distal engaging members 148.

FIG. 9 shows an exploded perspective view of outer member assembly 200 including outer member 202, reduction assembly 300, and locking assembly 400. FIGS. 10A-11C show extender assembly 200 in various assembled views. Outer member 202 includes tubular body portion 204 extending between a distal end portion 210 and proximal hub portion 230. Outer member 202 also defines a central bore 206 extending along longitudinal axis 102 and opening at distal end 205 and proximal end 207. Proximal hub portion 230 receives and is engaged to reduction assembly 300 in the proximal end opening of bore 206. Locking assembly 400 includes first and second locking members 402, 404 engaged to opposite sides of proximal hub portion 230.

Reduction assembly 300 includes first and second bearing assemblies 302, 304 and actuation member 310. Actuation member 310 includes a distal cylinder portion 312, a proximal engaging portion 314, and a central flange 316 extending radially outwardly from and between portions 312, 314. Central flange 316 extends circumferentially around actuation member 310. Actuation member 310 also includes an inner bore 318 extending between and opening at the proximal and distal ends of actuation member 310. The inner surface of actuation member 310 defines an internal thread profile 320 therealong between the distal and proximal ends of actuation member 310. Distal cylinder portion 312 includes a number of windows 322 spaced circumferentially thereabout. In the illustrated embodiment, four windows 322 are provided that are spaced 90 degrees from one another about the circumference of cylinder portion 312. Reduction assembly 300 also includes a retaining flange 324.

Figure 11B:
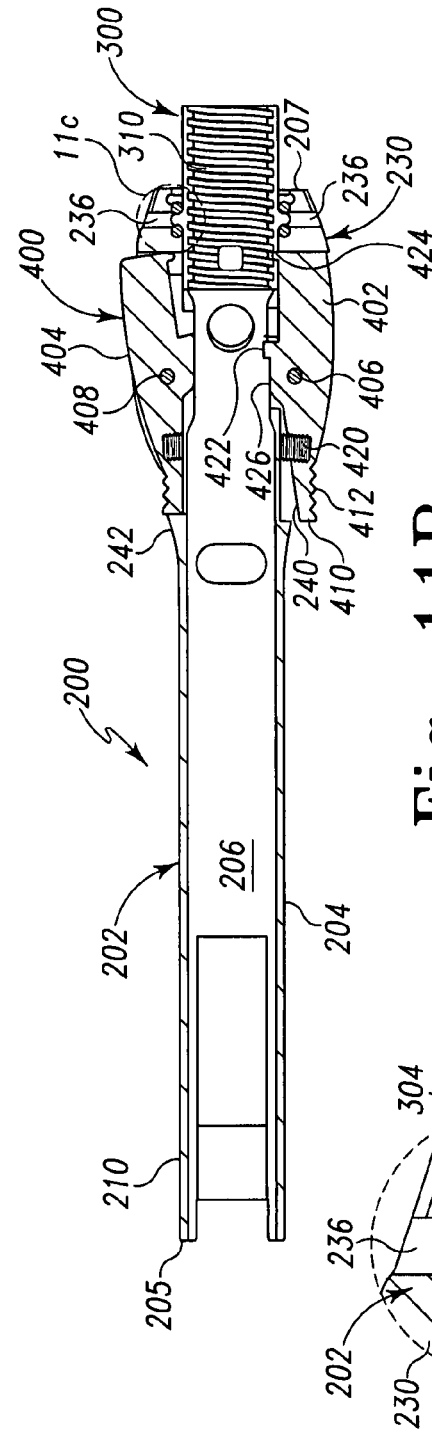
FIG. 11B is a section view along line 11B-11B of FIG. 11A-11A.
Figure 11C:
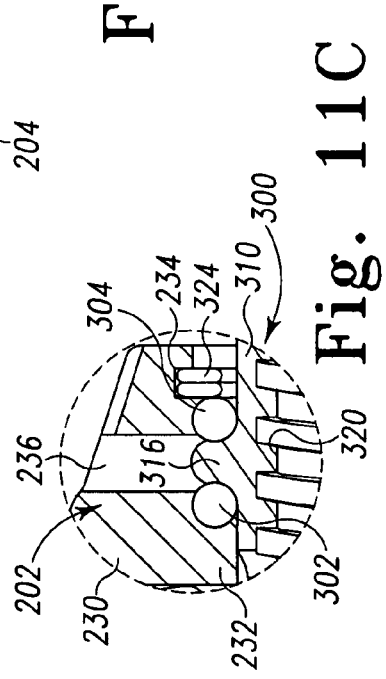
FIG. 11C is an enlarged detail view of area 11C in FIG. 11B.
Figure 15A:
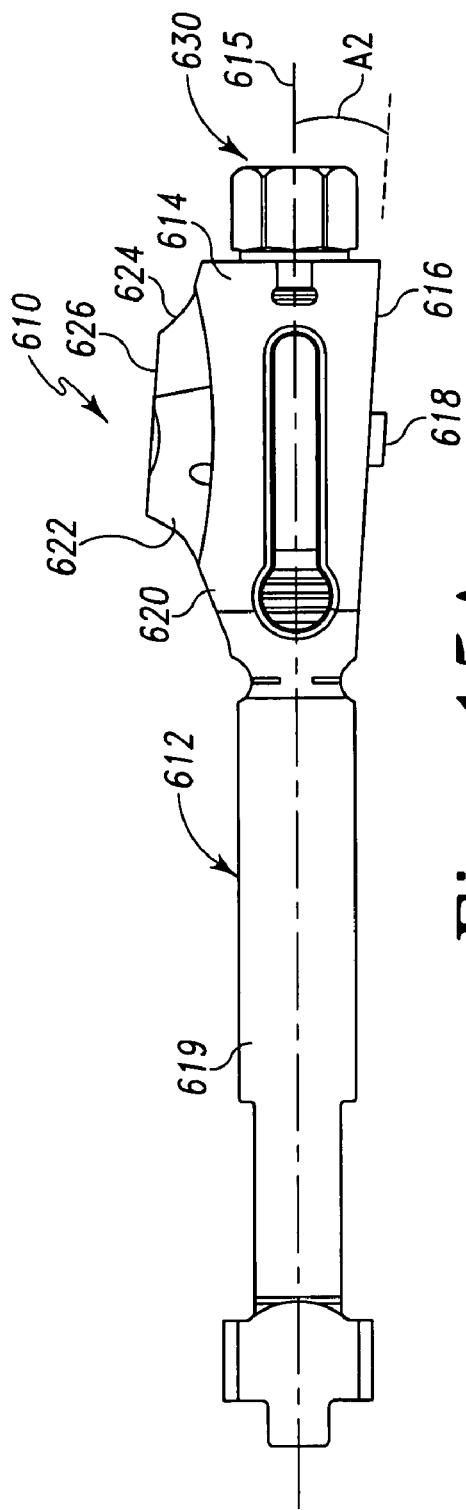
FIG. 15A is an elevation view of another embodiment outer member assembly.
Figure 15B:
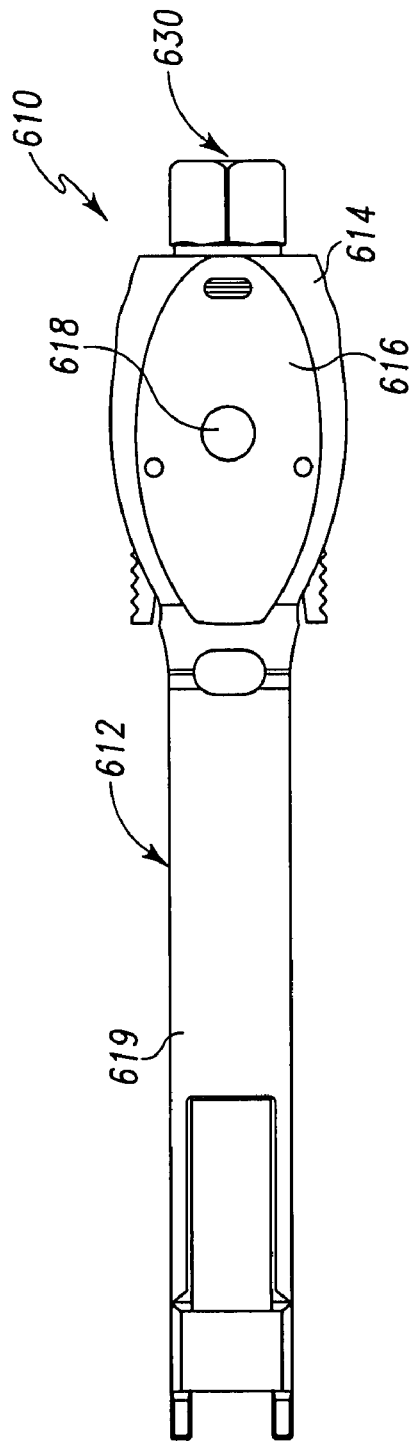
FIG. 15B is an elevation view of the outer member assembly of FIG. 15A rotated 90 degrees about its longitudinal axis.
Figure 16A:
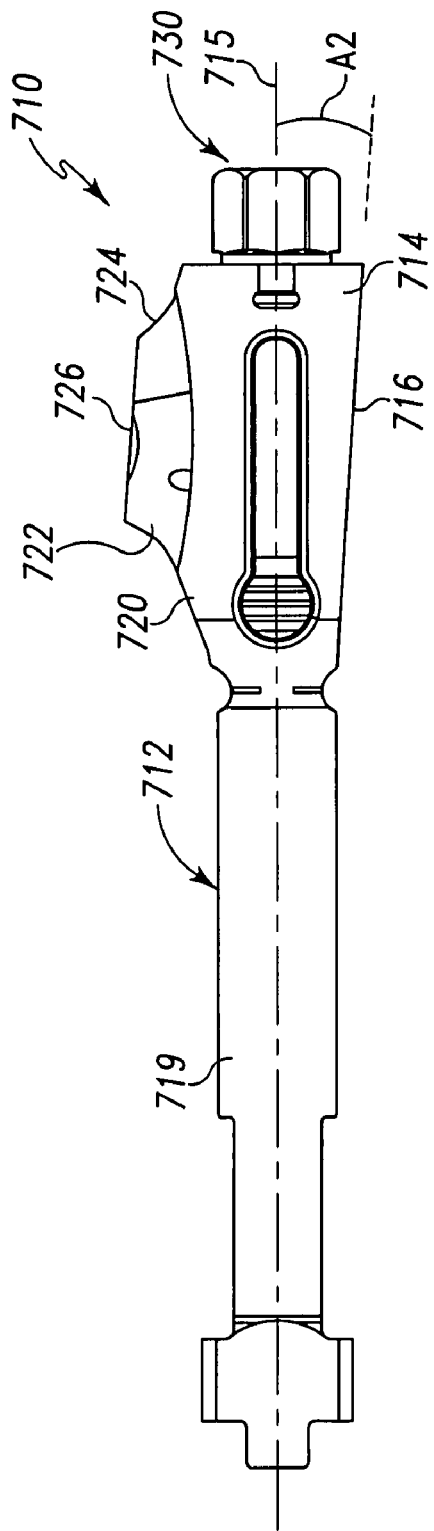
FIG. 16A is an elevation view of another embodiment outer member assembly.
Figure 16B:
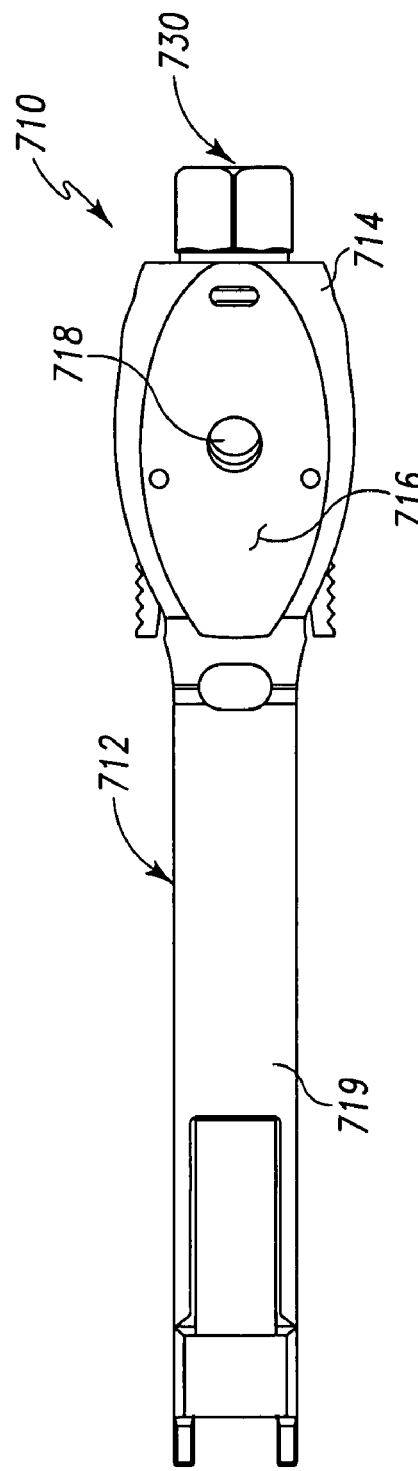
FIG. 16B is an elevation view of the outer member assembly of FIG. 16A rotated 90 degrees about its longitudinal axis.

As shown in FIGS. 11B-11C, reduction assembly 300 is assembled to outer member 202 by positioning sleeve portion 312 of actuation member 310 in bore 206. Outer member 202 includes an internal lip 232 extending into bore 206. First bearing assembly 302 is positioned adjacent to lip 232, and actuation member 310 is positioned with flange 316 proximal of first bearing assembly 302. Second bearing assembly 304 is positioned proximal of ring 316, and retaining flange 324 is positioned proximally of second bearing assembly 304. Retaining flange 324 is received in a circumferential groove 234 extending around bore 206 of outer member 202. Retaining flange 324 extends into bore 206 to overlap second bearing assembly 304 and retain actuation member 310 in axial position relative thereto while bearing assemblies 302, 304 facilitate rotation of actuation member 310 about longitudinal axis 102 of extender 100. Inner thread profile 320 is configured to threadingly engage externally threaded end portion 116 of inner member 110 so that rotation of actuation member 310 axially displaces inner member 110 relative to outer member 202.

In one embodiment, retaining flange 324 is a split ring that is circumferentially bendable to reduce and expand its diameter to facilitate insertion into and engagement with outer member 202 in groove 234. Outer member 202 also include a number of holes 236, as also shown in FIG. 13C, spaced thereabout in communication with bore 206 that provide access to bearing assemblies 302, 304 for maintenance and cleaning.

Hub portion 230 includes opposite first and second locking member receptacles 240, 242 (also shown in FIG. 13B) on opposite sides thereof. Receptacles 240, 242 extend from the outer surface of hub portion 230 and communicate with bore 206. First and second locking members 402, 404 of locking assembly 400 are received in respective ones of the locking member receptacles 240, 242. First and second coupling pins 406, 408 pivotally couple respective ones of the first and second locking members 402, 404 to hub portion 230, as shown in FIGS. 10B and 11B.

Locking members 402, 404 are identical to one another, and will be further described with reference to locking member 402, it being understood that locking member 404 includes the same features. Locking member 402 includes a distal end portion 410 with an outer roughened surface 412 to facilitate non-slipping engagement with the thumb or finger of the user. Locking member 402 also includes a lateral bore 414 to receive first coupling pin 406 therethrough. The inner side 416 of locking member 402 includes a well 418 to receive biasing member 420. Biasing member 420 normally biases distal end portion 410 away from bore 206 about the pivoting coupling location with coupling pin 406, as shown in FIG. 11B. Second locking member 404 is similarly coupled to the opposite side of hub portion 230 with biasing member 421 biasing the distal portion of locking member 404 away from bore 206. Biasing members 420, 421 contact lip 238 (FIG. 13B) of outer member 202, and extend between outer member 202 and the well of the respective locking member 402, 404.

Inner side 416 of locking member 402 also includes a ratchet tooth 422 extending therefrom that is located slightly proximally of lateral bore 414, and a proximal tooth 424 extending therefrom that is located at the proximal end of locking member 402. In the unlocked position shown in FIGS. 3A-3C and FIGS. 5A-5C, (the unlocked position is also shown in FIGS. 10A and 11B with respect to locking member 404) ratchet tooth 422 includes a cam portion 426 providing a ramped surface that resides in groove 126 along and in contact with inner member 110, compressing biasing member 420 and orienting proximal tooth 424 away from actuation member 310. Ratchet tooth 422 is also pivoted away from inner member 110 so that its tooth portion is displaced from windows 128a, 128b. In the locked and engaged position of FIGS. 4A-4C (the locked position is also shown with respect to locking member 402 in FIGS. 10A and 11B) the tooth portion of ratchet tooth 422 is positioned in distal window 128b of inner member 110. Locking member 402 pivots about its pivotal connection with hub portion 230 to position proximal tooth 424 in one of the windows 322 about actuation member 310. Teeth 422, 424 prevent inner member 110 from moving distally relative to outer member 202, which would release the anchor 50 engaged to inner member 110. If it is desired to release anchor 50, locking members 402, 404 are depressed at their respective distal end portions 410 against the bias of biasing members 420, 421 to move respective teeth 422, 424 out of the respective windows 128b, 322, allowing inner member 110 to axially move distally relative to outer member 202 to release anchor 50 by manipulating actuation member 310.

Ratchet tooth 422 includes sloped, distally oriented cam portion 426 that contacts inner member 110 in groove 126 so that rotation of actuation member 310 in a first direction proximally displaces inner member 110 relative to outer member 202 from the locked position of FIGS. 4A-4C toward the reduced positions of FIGS. 5A-5C. This proximal displacement pivots locking member 402 to remove the tooth portion of ratchet tooth 422 from distal window 128b against the bias of biasing member 420, thereby also displacing proximal tooth 424 out of window 322 of actuation member 322. In this unlocked position, cam portion 426 resides along groove 126 of inner member 110, as shown in FIGS. 5A-5C. Engagement of anchor 50 with inner member 110 is maintained by the distal portion 210 in engagement with distal shoulders 146 of arms 130, 132 of inner member 110. Rotation of actuation member 310 in the opposite direction to distally displace inner member 110 relative to outer member 202 is prevented by engagement of ratchet tooth 422 with inner member 110 and engagement of proximal tooth 424 with actuation member 310.

Proximal window 128a of inner member 110 provides a locked and open condition for inner member 110 where arms 130, 132 of inner member 110 are spaced to receive anchor 50 therebetween but inner member 110 is prevented from moving distally relative to outer member 202 to the fully extended position of FIGS. 3A-3C. In the locked and open condition, proximal window 128a receives ratchet tooth 422 to lock the axial positioning of inner member 110 relative to outer member 202. Since the relative axial positioning of actuation member 310 and outer member 202 remains the same, proximal tooth 424 is received in an aligned one of the windows 322 of actuation member 310 in the locked and open position. From this locked and open position, actuation member 310 is rotatable to proximally displace inner member 110 from the locked and open position to the locked and engaged position of FIGS. 4A-4C, where ratchet tooth 422 engages distal window 128b to maintain inner member 110 in engagement with anchor 50. However, ratchet tooth 422 prevents actuation member 310 from being rotated in the opposite direction to distally displace inner member 110 relative to outer member 202 unless locking members 402, 404 are moved to the unlocked position.

Hub portion 230 also includes a male extension 244 extending from abutment surface 245 on one side thereof and a female receptacle 246 in mounting surface 249 on the opposite side thereof. Female receptacle 246 receives a pin or other projection from an installation instrument, such as installation instrument 20 discussed above. Male extension 244 is positionable into a receptacle of an adjacent extender, such as female receptacle 522 of middle extender 500, also discussed above. As shown in FIG. 12B, male extension 244 and female receptacle 246 are aligned along pivot axis 247 about which the installation instrument pivots when mounted thereto. Other embodiments contemplate hub portion 230 is configured like any of the hub portions discussed herein with respect to extenders 500, 600 and 700. In still other embodiments, the hub portion does not include any male extension and/or female receptacle.

Body portion 204 includes a port 250 extending therethrough in communication with bore 206. An aligned portion of indicia 118 of inner member 110 is viewable by the surgeon or other attendant through port 250 so that the relative positioning of inner member 110 and outer member 202 can be readily determined. For example, the indicia 118 can indicate the fully extended position of FIGS. 3A-3C, the locked and open position where ratchet tooth 422 engages proximal window 128a of inner member 110, and the locked and engaged position of FIGS. 4A-4C. Indicia 118 can also provide increments of the reduction distance as inner member 110 is displaced between the position of FIGS. 4A-4C and the fully reduced position of FIGS. 5A-5C. The surgeon can readily determine the amount of reduction that has been attained even when the anchor and bony segment are not readily viewable such as during a minimally invasive procedure.

Distal portion 210 of outer member 202 will be described further with reference to FIGS. 12A to 13C. Distal portion 210 includes distal fingers 212, 213 extending distally from a collar 214. Collar 214 extends around bore 206. Opposite fixed arms 216, 217 extend proximally from collar 214 to body portion 204. Arms 216, 217 define opposite sides of openings 218, 219. Openings 218, 219 extend between collar 214 and body portion 204, and open into bore 206.

Collar 214 includes concavely curved inner surfaces 220, 221 that are shaped to ride along and slidably contact distal shoulders 246 of arms 130, 132 of inner member 110. Collar 214 maintains contact with distal shoulders 246 from the locked and engaged position of FIGS. 4A-4C to the fully reduced position of FIGS. 5A-5C so that arms 130, 132 of inner member 110 do not release anchor 50 clamped between engaging members 148 of inner member 110.

Fingers 212, 213 reside between arms 130, 132 and along slot 138 of inner member 110. As shown in FIG. 12D, fingers 212, 213 include concavely curved inner surfaces 222, 223 that form an extension portion of bore 206 to accommodate placement and rotation of a set screw, screw driver or other rotational instrument or device therebetween. In the fully reduced position shown in FIGS. 5A-5C, fingers 212, 213 extend between engaging members 148 of arms 130, 132 to force or reduce connecting element 30 into receiving portion 54 of anchor 50. In the engaged position of FIGS. 4A-4C, fingers 212, 213 are spaced proximally from proximal end 58 of anchor 50 so that pathway 104 is unobstructed to accommodate insertion of a connecting element 30 proximally of proximal end 58 for subsequent reduction into receiving portion 54 of anchor 50.

As shown in FIGS. 6-7, arms 130, 132 include outer flats 131, 133, respectively, that extend along opposite outer sides of each arm 130, 132 adjacent to slot 138. Flats 131, 133 contact inner flats 224, 225, shown in FIG. 12D, along the inner surface of collar 214, providing anti-rotation features that resist inner member 110 from rotating axially in outer member 202. The positioning of cam surface 426 of ratchet teeth 422 in the respective grooves 126 of inner member 110 also prevents inner member 110 from rotating about longitudinal axis 102 in outer member 202.

As shown in FIG. 12D, collar 214 further includes four ledges 228a, 228b, 228c, 228d positioned thereabout in collar 214 that contact respective ones the four bosses 156a, 156b associated with arms 130, 132 as arms 130, 132 move through collar 214. Each of the bosses 156a, 156b rides along a respective adjacent edge of arms 216, 217 when extender 100 is engaged to the anchor, as shown in FIGS. 4A-5C. When in the locked and open condition and when moving toward the fully extended position shown in FIGS. 3A-3C, bosses 156a, 156b are positioned in collar 214 and contact the proximal ramped portion 229 (FIG. 12C) of an aligned one of the proximal ramped portion 229 in collar 214 to force arms 130, 132 away from one another and provide sufficient force to remove projections 150 from their position in the recesses of the arms of anchor 50, ensuring that anchor 50 is ejected and uncoupled from inner member 110 when extender 100 and anchor 50 are located within the patient.

While the invention has been illustrated and described in detail in the drawings and foregoing description, the same is to be considered as illustrative and not restrictive in character.

All changes and modifications that come within the spirit of the invention are desired to be protected.

What is claimed is:

1. A surgical instrument assembly, comprising:
at least one anchor including a bone engaging portion and a proximal receiving portion;
an extender including an outer member and an inner member within a bore of said outer member, said inner and outer members being elongated and extending along a longitudinal axis, said extender further comprising a reduction assembly including:
an actuation member rotatably mounted to a proximal end of said outer member and threadingly engaged to a proximal end portion of said inner member, wherein said actuation member is operable to axially move said inner and outer members relative to one another to move a distal end of said outer member and said proximal receiving portion toward one another when said inner member is engaged to said proximal receiving portion; and
said outer member includes a port allowing visualization therethrough and said inner member includes indicia viewable through said port to provide an indication of an axial position of said inner member relative to said outer member,
wherein
said outer member includes a proximal hub portion and a tubular body portion extending distally from said proximal hub portion;
said actuation member includes a distal sleeve portion, a proximal engaging portion, and a circumferential flange therebetween projecting radially outwardly, wherein said distal sleeve portion is received in said bore of said outer member in said proximal hub portion; and
said reduction assembly includes a first bearing assembly between said outer member and a distal side of said flange and a second bearing assembly between said outer member and a proximal side of said flange.

2. The assembly of claim 1, wherein said proximal end portion of said inner member includes an external thread profile and said actuation member includes an inner thread profile threadingly engaged to said external thread profile.

3. The assembly of claim 2, wherein said inner member includes an elongated groove in an outer surface thereof extending along said longitudinal axis and interrupting said external thread profile.

4. The assembly of claim 1, wherein said inner member includes a pair of arms extending distally from said proximal end portion, said pair of arms being movable toward and away from one another to selectively grip and release said proximal receiving portion of said anchor therebetween.

5. A surgical instrument assembly, comprising:
at least one anchor including a bone engaging portion and a proximal receiving portion;
an extender including an outer member and an inner member within a bore of said outer member, said inner and outer members being elongated and extending along a longitudinal axis, said extender further comprising a reduction assembly including:
an actuation member rotatably mounted to a proximal end of said outer member and threadingly engaged to a proximal end portion of said inner member, wherein said actuation member is operable to axially move said inner and outer members relative to one another to move a distal end of said outer member and said proximal receiving portion toward one another when said inner member is engaged to said proximal receiving portion; and
said outer member includes a port allowing visualization therethrough and said inner member includes indicia viewable through said port to provide an indication of an axial position of said inner member relative to said outer member;
wherein said proximal end portion of said inner member includes an external thread profile and said actuation member includes an inner thread profile threadingly engaged to said external thread profile;
wherein said inner member includes an elongated groove in an outer surface thereof extending along said longitudinal axis and interrupting said external thread profile; and
further wherein
said inner member defines an internal passage extending along said longitudinal axis and opening at a proximal end of said inner member and a distal end of said pair of arms;
said inner member defines a window in said groove opening into said passage; and
said extender includes a locking assembly with at least one locking member pivotally mounted to a proximal hub portion of said outer member about a pivot axis, said locking member including an end tooth at one end thereof remote from said pivot axis and a ratchet tooth extending therefrom adjacent said pivot axis, wherein in an unlocked position said locking member is pivoted about said pivot axis with said end tooth and said ratchet tooth disengaged from said inner member and in a locked position said end tooth engages said actuation member and said ratchet tooth is received in said window of said inner member.

6. The assembly of claim 5, wherein:
said inner member includes a second groove in said proximal body portion extending along said longitudinal axis and in said external thread profile of said inner member, said inner member further including a second window in said second groove in communication with said passage; and
said locking assembly includes a second locking member on a side of said proximal hub portion opposite said at least one locking member, said second locking member being pivotally mounted to said proximal hub portion about a second pivot axis, said second locking member including a second end tooth at one end thereof remote from said second pivot axis and a second ratchet tooth extending therefrom adjacent said second pivot axis, wherein in an unlocked position said second locking member is pivoted about said second pivot axis with said second end tooth and said second ratchet tooth disengaged from said inner member and in a locked position said second end tooth engages said actuation member and said second ratchet tooth is received in said second window of said inner member.

7. The assembly of claim 5, wherein said ratchet tooth includes a tooth portion and a cam portion extending from said tooth portion, said cam portion riding in said groove in said unlocked position to resist rotation of said inner member in said outer member as said inner and outer members are axially moved relative to one another.

8. The assembly of claim 5, wherein said inner member includes a second window space proximally from said window, said second window being located in said groove and in communication with said passage.

9. A surgical instrument assembly, comprising:

at least one anchor including a bone engaging portion and a proximal receiving portion;

an extender including an outer member and an inner member within a bore of said outer member, said inner and outer members being elongated and extending along a longitudinal axis, wherein said outer member includes a proximal hub portion, a tubular body portion extending distally from said proximal hub portion, and a distal collar portion, and said inner member includes a proximal body portion including an external thread profile and a pair of arms extending distally from said proximal body portion, said pair of arms being movable toward one another to grip said proximal receiving portion of said anchor therebetween, said extender further comprising a reduction assembly including:

an actuation member rotatably mounted to a proximal end of said outer member and threadingly engaged to said external thread profile of said inner member, wherein said actuation member is operable to axially move said inner and outer members relative to one another to move a distal end of said outer member and said proximal receiving portion toward one another when said inner member is engaged to said proximal receiving portion; and a locking assembly with at least one locking member pivotally mounted to said proximal hub portion about a pivot axis, said locking member including an end tooth at one end thereof remote from said pivot axis and a ratchet tooth extending therefrom adjacent said pivot axis, wherein in an unlocked position said locking member is pivoted about said pivot axis with said end tooth and said ratchet tooth disengaged from said inner member and in a locked position said end tooth engages said actuation member and said ratchet tooth engages said inner member.

10. The assembly of claim 9, wherein:

said pair of arms of said inner member define a slot therebetween; and said outer member includes a first and second fingers on opposite sides of said collar that extend distally from said collar, said first and second fingers being located between said pair of arms of said inner member along said slot.

11. The assembly of claim 10, wherein said outer member includes a pair of arms extending proximally from said collar to said tubular body portion, said pair of arms defining openings into said outer member on opposite sides of said outer member.

12. The assembly of claim 11, wherein each of said pair of arms of said inner member includes a pair of bosses at a proximal end thereof, said pair of bosses extending outwardly from said respective arm and being movable along an adjacent edge of said pair of arms of said outer member as said inner member is moved axially relative to said outer member.

13. The assembly of claim 12, wherein said collar includes an inner surface profile defining a number of ledges extending longitudinally from a proximal end of said collar toward a distal end of said collar, each of said ledges including a proximal ramped portion tapering toward said longitudinal axis to said edge of an adjacent one of said arms of said outer member.

14. The assembly of claim 13, wherein as said bosses move along respective ones of said proximal ramped portions said collar of said outer member said arms of said inner member are forced away from one another.

15. The assembly of claim 9, wherein said outer member includes a distal collar and said pair of arms of said inner member each include flat surfaces along opposite sides thereof, said flat surfaces engaging flat surfaces in said collar to resist said inner member from rotating relative to said outer member.

16. The assembly of claim 9, wherein:

said inner member includes a longitudinal groove extending along said proximal body portion in said external thread profile, said inner member further including a window in said groove; and said ratchet tooth is received in said window in said locked position.

17. The assembly of claim 16, wherein said locking member is biased with said ratchet tooth configured so that said ratchet tooth prevents said inner member from moving distally relative to said outer member when in said locked position and said ratchet tooth is configured so that rotation of said actuation member to proximally displace said inner member relative to said outer member pivots said locking member against said bias and displaces said ratchet tooth from said window.

* * * * *